United States Patent
Turcott

(12) 
(10) Patent No.: US 6,477,406 B1
(45) Date of Patent: Nov. 5, 2002

(54) EXTRAVASCULAR HEMODYNAMIC ACOUSTIC SENSOR

(75) Inventor: Robert Turcott, Menlo Park, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 09/543,394

(22) Filed: Apr. 5, 2000

Related U.S. Application Data

(63) Continuation-in-part of application No. 09/467,298, filed on Dec. 17, 1999, which is a continuation-in-part of application No. 09/438,017, filed on Nov. 10, 1999.

(51) Int. Cl.⁷ .................................................. A61B 5/00
(52) U.S. Cl. ........................................ 600/518; 607/36
(58) Field of Search ............................ 600/518; 607/17, 607/36

(56) References Cited

U.S. PATENT DOCUMENTS

| | | | |
|---|---|---|---|
| 3,985,121 A | 10/1976 | Hellenbrand | 128/2 K |
| 4,356,827 A | 11/1982 | Uemura et al. | 128/680 |
| 4,763,646 A | 8/1988 | Lekholm | 128/419 PG |
| 4,774,950 A | 10/1988 | Cohen | 128/419 D |
| 5,040,533 A | 8/1991 | Fearnot | 128/419 PG |
| 5,334,222 A | 8/1994 | Salo et al. | 607/17 |
| 5,540,727 A | 7/1996 | Tockman et al. | 607/18 |
| 5,554,177 A | 9/1996 | Kieval et al. | 607/17 |
| 5,685,317 A | 11/1997 | Sjostrom | 128/715 |
| 5,687,738 A | 11/1997 | Shapiro et al. | 128/715 |
| 5,700,283 A * | 12/1997 | Salo | 607/17 |
| 5,702,427 A * | 12/1997 | Ecker et al. | 607/28 |
| 5,888,187 A * | 3/1999 | Jaeger et al. | 600/23 |
| 5,935,081 A | 8/1999 | Kadhiresan | 600/513 |
| 6,044,299 A * | 3/2000 | Nilsson | 607/19 |
| 6,223,081 B1 * | 4/2001 | Kerver | 607/17 |

OTHER PUBLICATIONS

Cohen, et al., "A Hemodynamically Responsive Antitachycardia system", Circulation, vol. 82, No. 2, Aug. 1990, pp. 394–406.

* cited by examiner

Primary Examiner—Carl Layno
(74) Attorney, Agent, or Firm—Steven M. Mitchell

(57) ABSTRACT

An implantable medical device such as a pacemaker or implantable cardioverter defibrillator or stand-alone hemodynamic monitor that uses an acoustic transducer responsive to heart sounds to detect the hemodynamic status of a patient. A hermetic housing encloses the device electronics and the device housing includes at least one substantially planar face configured to act as a diaphragm in response to acoustic waves. A transducer positioned inside the device housing provides an output signal to the device electronics responsive to vibration of the diaphragm. Embodiments of the transducer include a piezoelectric element and laser interferometer. The hemodynamic information may be used in various ways including arrhythmia discrimination and pacing and sensing optimization.

10 Claims, 13 Drawing Sheets

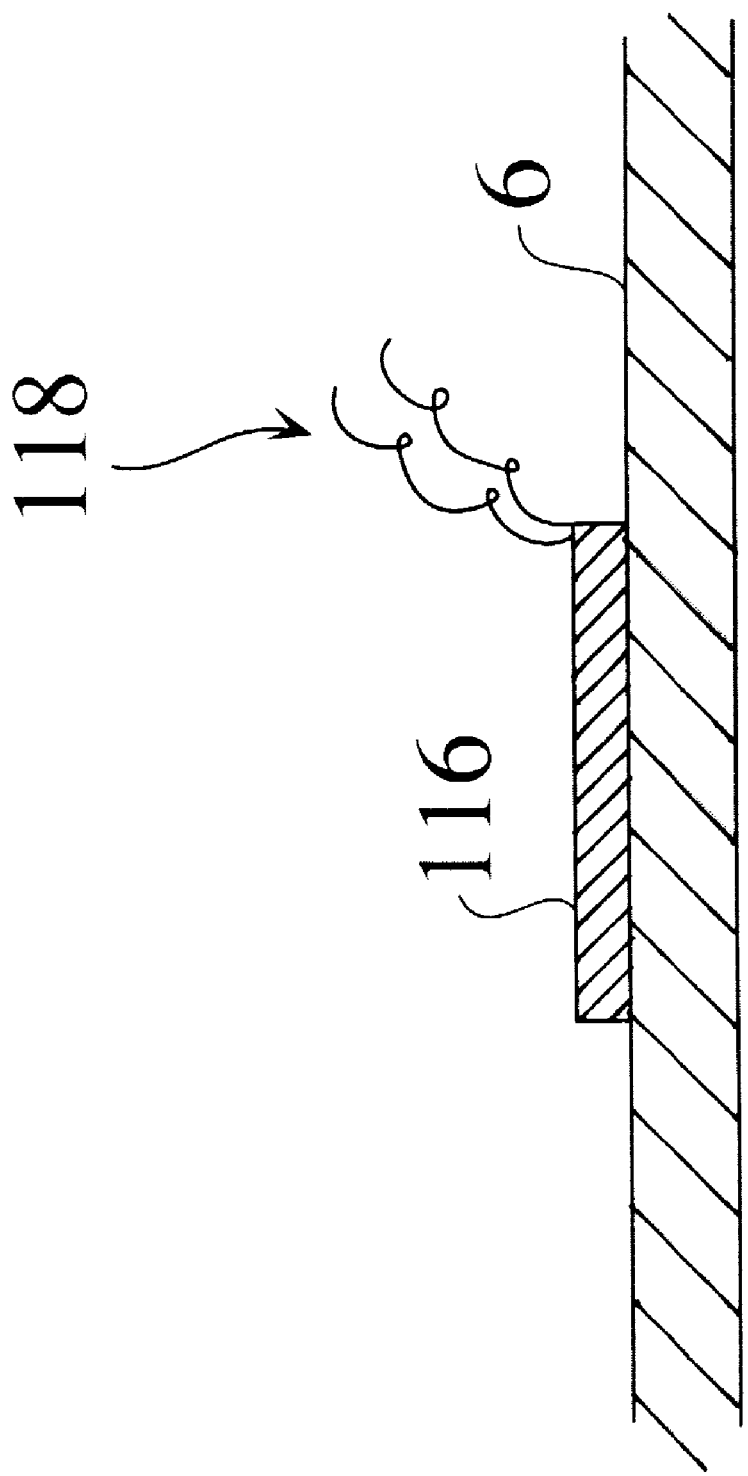

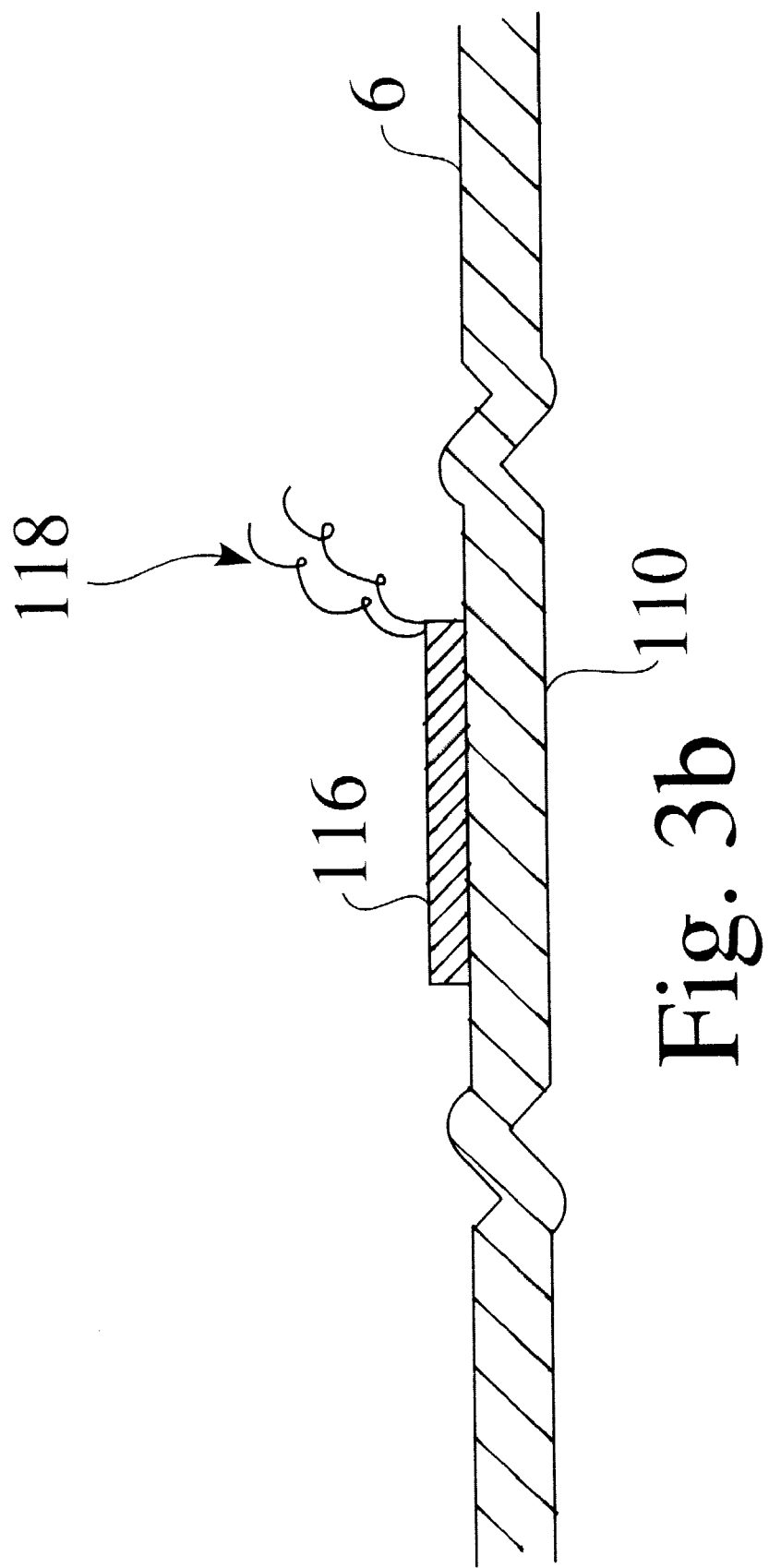

EXTRAVASCULAR HEMODYNAMIC ACOUSTIC SENSOR

This is a continuation-in-part of application Ser. No. 09/467,298, filed Dec. 17, 1999 which is a continuation-in-part of application Ser. No. 09/438,017, filed Nov. 10, 1999.

BACKGROUND OF THE INVENTION

I. Field of the Invention

This invention relates generally to cardiac devices, and more particularly to the assessment of hemodynamic status by a cardiac device.

II. Description of the Related Art

A critical function of implantable cardioverter defibrillators (ICDs) is to identify and terminate hemodynamically unstable arrhythmias such as ventricular fibrillation (VF) and ventricular tachycardia (VT). A technical challenge is to achieve high sensitivity, so that the occurrence of such arrhythmias does not go undetected, while maximizing specificity, so that relatively benign rhythms such as atrial fibrillation (AF) and sinus tachycardia (ST) are not treated.

Conventional implantable cardioverter defibrillators (ICDs) perform discrimination through analysis of the intracardiac electrogram, where features such as rate, interval regularity, and QRS morphology are analyzed in order to identify the underlying rhythm. This approach is convenient because electrical sensing can be easily performed using the same leads that the device requires to deliver therapy. Furthermore, electrogram features provide reasonable accuracy in rhythm identification. However, the accuracy of this approach is ultimately limited because there are inherent ambiguities in cardiac electrical activity that prevent perfect identification. For example, VT, which typically generates a wide QRS complex morphology and regular intervals, may exhibit narrow complexes, particularly if bipolar sensing is used, and irregular intervals. On the other hand, AF, which typically generates narrow QRS complexes and irregular intervals, may exhibit a wide QRS complex, due to a fixed- or rate-related bundle branch block or interventricular conduction defect. In addition AF may produce extended sequences of regular intervals. Thus, there is a theoretical limit to the accuracy with which electrogram analysis can identify cardiac rhythms. The problem is compounded by the fact that practical considerations, such as power consumption and manufacturing costs, impose compromises in the algorithms and sensing configurations that are implemented.

The conventional approach to the detection of pathological arrhythmias using electrogram analysis rests on the premise that the type of therapy is appropriately determined by the underlying cardiac rhythm. In fact, from a clinical perspective, a more important criterion for determining therapy than the identification of the underlying rhythm is whether the rhythm is hemodynamically stable, that is, whether the heart is pumping blood sufficiently to ensure adequate perfusion of vital organs. For example, there are forms of VT that are hemodynamically stable which do not require immediate cardioversion. For these rhythms, low energy methods of termination such as anti-tachycardia pacing can be attempted without sacrificing safety. Such an approach improves device longevity, and avoids subjecting the conscious patient to painful and distressing electrical shocks. Conversely, there are cases of AF and supraventricular tachycardias that are hemodynamically unstable because of high rate or poor ventricular function, and therefore require rapid termination. Thus, the most relevant question clinically is not the identification of the underlying cardiac rhythm but rather whether the rhythm is hemodynamically stable. This point is well illustrated by the Universal Algorithm for emergency cardiac care, advocated by the American Heart Association, and described in the book Advanced Cardiac Life Support, R. O. Cummins, Ed., 1997. The major branch point, which occurs early in the algorithm, is the test for the presence of an arterial pulse, a rapid and robust method of assessing hemodynamic status. Subsequent evaluation and treatment along the two branches of the algorithm varies significantly depending on the outcome of this test. Only later in the algorithm is identification of the origin, ventricular vs. supraventricular, of the cardiac rhythm attempted.

Because of the inherent limitation in the accuracy that can be achieved in identifying cardiac rhythms using electrogram analysis, and more importantly, because what is of ultimate clinical relevance is the hemodynamic status of the patient, what is needed is a method and apparatus for rapidly assessing hemodynamic status that can be used by implantable cardiac devices.

Another application of rapid hemodynamic status assessment is in capture verification, a technique that verifies that a pacemaker-delivered stimulus has electrically captured the myocardium and initiated the propagation of a depolarization. The technique is useful because it allows continuous or periodic adjustment of the pacing energy to accommodate a changing threshold. It allows the pacemaker to deliver the minimum energy necessary to consistently capture the heart, which both maximizes the pacemaker longevity and enhances patient safety. A method of capture verification that is known in the art analyzes the electrical evoked response that is generated after a pace stimulus is delivered by the pacemaker. While this approach, disclosed in U.S. Pat. Nos. 5,165,404 and 5,165,405, has proven to be commercially viable, it requires sophisticated circuitry and low-polarization leads, and is potentially susceptible to electrical noise. It would be advantageous to have a capture verification technique based on hemodynamic status assessment.

One of the challenges of electrically detecting cardiac depolarizations is ensuring that the system is sufficiently sensitive so that myocardial depolarizations are recognized by the device, while at the same time not excessively sensitive so that repolarization waves or noise, such as that induced by diaphragmatic myopotentials, is incorrectly interpreted as a depolarization. Beat-to-beat hemodynamic sensing would allow oversensing of electrical noise to be recognized and distinguished from ventricular fibrillation (VF) or tachycardia. In oversensing of electrical noise, regular and robust mechanical cardiac contractions would occur along with higher-rate ventricular sensed events. In this case the sensitivity could be decreased until the ventricular sensed events occurred in concert with cardiac contractions. On the other hand, the detection of robust mechanical cardiac contractions during the absence of ventricular sensed events would indicate that the sense amplifier sensitivity is set too low and should be increased. Finally, the presence of rapid ventricular sensed events without detected cardiac contractions would indicate the presence of VF, hemodynamically unstable VT, or another hemodynamically unstable rhythm. It would thus be advantageous to provide an improved system for verification of sensed events and optimization of sensing thresholds.

Yet another application of hemodynamic sensing is in pace-parameter optimization, in which any of a number of parameters that define pacing characteristics is optimized. Pace-parameter optimization is particularly applicable to multi-site pacing. For example, in dual-chamber (atrial and ventricular) pacemakers the atrio-ventricular (AV) delay is optimized, so that the ventricular contraction is timed such that the contribution of the atrial contraction is maximally exploited. Another example is biventricular pacing for heart failure, in which ventricular synchrony is optimized by adjusting the timing that pace pulses are delivered to various sites. Currently, these parameters are set to default nominal values, or labor-intensive methods are used to assess hemodynamics in order to optimize the parameters at time of device implant. Examples of these methods include ultrasound to measure ejection fraction and left heart catheterization to measure the rate of change of left ventricular pressure during systole, which is a measure of contractility and mechanical efficiency. In addition to the substantial time and effort these approaches impose, the invasive techniques increase the perioperative risk to the patient. Furthermore, these approaches are possible only during device implant or follow-up examinations. A hemodynamic sensor incorporated into the device would allow frequent and dynamic optimization of pacing parameters.

In pace-parameter optimization, some measure of cardiac function is needed to serve as the feedback which determines how the pace parameters are adjusted. The measure of cardiac function provides the basis of optimization; it allows one set of parameter values to be deemed superior to another. To be fully general the measure must operate over short time scales, ideally on a beat-to-beat basis. While a slower response may be adequate for adjusting, for example, the overall pacing rate, a rapid response is necessary to dynamically adjust multi-site timing to changes in body posture, which is particularly important for certain diseases such as hypertrophic obstructive cardiomyopathy and dilated cardiomyopathy. Furthermore, a sensor capable of detecting changes in hemodynamic parameters on a beat-to-beat basis would allow the optimization algorithm to achieve the ideal parameter values quickly.

Still another application that would benefit from hemodynamic sensing is in the monitoring of disease status in heart failure patients. Hemodynamic sensing would allow the optimization of medical management of the heart failure patient. It would also allow the early recognition of a developing acute exacerbation. With early recognition the exacerbation could be relatively easily terminated, before it becomes fully developed and requires hospitalization and intensive intervention to terminate.

A further application of hemodynamic sensing is in the assessment of autonomic status. For example, the development of diabetic neuropathy is known to adversely affect the sympathetic/parasympathetic balance and the body's response to autonomic perturbations. Since the control of cardiovascular system is in large part the responsibility of the autonomic nervous system, sensitive hemodynamic measurements can detect changes in autonomic tone, such as parasympathetic decline associated with the development of diabetic neuropathy or the sympathetic enhancement provoked by a CHF exacerbation.

Techniques for hemodynamic assessment are known in the art. In the context of arrhythmia discrimination Cohen and Liem (Circ., 1990, 82:394–406) systematically studied the use of a pressure transducer placed in the right ventricle, a configuration described in U.S. Pat. No. 4,774,950, and demonstrated that this approach effectively discriminated hemodynamically stable from hemodynamically unstable cardiac rhythms. The approach of Cohen and Liem is advantageous in that it directly characterizes important hemodynamic variables, namely central venous pressure and the pressure differentials that the heart is able to generate. However, incorporation of a hemodynamic sensor into an intracardiac lead is undesirable for several reasons. First, it increases the cost of the lead, which because of the significant engineering challenges associated with providing chronic intracardiac placement, already represents a sizable fraction of the overall cost of the system. More importantly, incorporation of a special sensor in an otherwise general-purpose lead imposes expensive compatibility constraints: any device that would make use of the sensor must have the special-purpose lead implanted with it, and once the lead has been implanted, any subsequent device changes, such as for upgrade or battery depletion, must have hardware capable of interfacing with the special-purpose sensor. Finally, a special class of patients, such as some pediatric patients and patients with congenital cardiovascular malformations, require epicardial placement of leads; intracardiac placement is not possible for them. These patients would not benefit from a hemodynamic sensing method that requires intracardiac placement. It is therefore desirable to provide a method and apparatus for hemodynamic sensing that does not require special intracardiac or intravascular leads. Such an invention would avoid expensive, special purpose leads. Furthermore, it would avoid imposing expensive lead-device compatibility constraints.

Erickson and Bennett, in U.S. Pat. No. 5,176,137, propose placing a two-wavelength oxygen saturation sensor in the right ventricle of the heart. Their disclosure assumes that during hemodynamically stable rhythms the oxygen saturation in blood returning to the right ventricle is pulsatile, and that the pulsatile character of the saturation decreases during hemodynamically unstable rhythms. Their disclosure further assumes that the average saturation level of the blood returning to the right ventricle decreases during hemodynamically stable sinus and ventricular tachycardias but remains approximately constant during unstable rhythms. The intracardiac placement of their sensor carries the disadvantages described above. More importantly, while slow changes in venous oxygen saturation can be expected with certain rhythms, the amount of time required for blood to return to the right ventricle from the periphery is substantial, on the order of tens of seconds. This delay is even longer for hemodynamically unstable rhythms. Delaying ICD therapy by this amount of time would compromise patient safety. What is needed is a method of assessing hemodynamic status that is robust and rapid. Ideally the method operates on the time scale of a single cardiac cycle, i.e., on a beat-to-beat basis.

Other examples of oxygen sensors exist in the art. U.S. Pat. Nos. 4,399,820, 4,467,807, 4,815,469, and 5,040,538 all present oxygen saturation or partial pressure sensors placed in the right ventricle for rate responsive pacing, in which the pacing rate of the pacemaker is controlled based on the metabolic demand of the body, which is a form of hemodynamic assessment and pace-parameter optimization. Assuming arterial $O_2$ is constant, a fall in venous $O_2$ below a critical level implies that the cardiac output is not sufficient to meet metabolic demand. In this case, a pacing parameter, the pacing rate, is increased. The time scale of this process is on the order of tens of seconds, much greater than the beat-to-beat assessment that is necessary to perform arrhythmia discrimination, capture verification, sensing gain and threshold optimization, and rapid pace-parameter optimization. Furthermore, the intravascular placement carries the disadvantages discussed above.

In U.S. Pat. No. 5,540,727, Tockman et al. disclose an algorithm for optimizing pacing parameters, including pacing mode. They mention a number of examples of a variety of measures of hemodynamic status, including both implantable embodiments (cardiac output measured using impedance plethysmography of the right ventricular volume, and right ventricular pressure) and external embodiments (cardiac output measured using Doppler ultrasound, heart sounds, blood pressure, respiratory gas analysis, and pulse oximetry). External measurements of hemodynamic status are labor-intensive and can only be used during periodic follow-up examination. They are therefore not suitable for arrhythmia discrimination, dynamic pace-parameter optimization, sensitivity optimization, or capture verification. The measures they present for implantable embodiments all require right ventricular placement, and thus carry with them the disadvantages described above.

In U.S. Pat. No. 5,334,222, Salo et al. present a system tailored to heart failure patients that includes dual chamber (atrial and ventricular) pacing with defibrillation capability. An algorithm for optimizing AV delay is disclosed which uses information generated by a generic sensor of cardiac function. Particular embodiments of the sensor that are described include intracardiac impedance plethysmography to assess stroke volume and cardiac output, an intracardiac pressure transducer, and Doppler ultrasound to assess blood flow velocity. An additional modality that is described is heart sounds, though neither a physical embodiment of a heart sound sensor nor a method of using heart sound to obtain a measure of cardiac function are disclosed.

Methods of pace-parameter optimization have been proposed using non-hemodynamic surrogates, such as QRS width. In U.S. Pat. No. 5,527,347 Shelton and Warkentin adjust the AV delay such that QRS width is maximized. Their invention is tailored to patients with hypertrophic obstructive cardiomyopathy, in whom a thickened intraventricular septum obstructs the ejection of blood from the left ventricle during systole. Delivering a pre-excitation pulse to the right ventricular apex is thought to pull the septum toward the right side of the heart, thereby reducing the degree of obstruction. In the patent, maximizing the QRS width is claimed to provide the optimal AV delay.

In contrast to maximizing QRS width, minimizing the QRS width has been proposed in biventricular pacing for patients with dilated cardiomyopathy. In these patients, improving the synchrony of ventricular contractions is thought to improve cardiac function to a clinically significant degree. QRS width serves as a marker for the degree of synchrony. However, recent results of Kass et al. (*Circ.* 1999; 99:1567–1573) showed that in heart failure patients QRS width tends to increase in VDD pacing, regardless of the pacing site and despite the significantly improved hemodynamic performance in some of the pacing configurations they tested. Thus the suitability of QRS width as a hemodynamic surrogate is suspect in this patient population.

Use of the QRS width as a feedback variable in pace-parameter optimization schemes such as those just described is convenient because the intracardiac or far-field electrogram is readily available. However, while the rationale for using QRS width in special settings of pace-parameter optimization is intuitively appealing, QRS width is not itself a measure of hemodynamic function, which is what would ideally be optimized in pace-parameter adjustment. Furthermore, while QRS width can provide useful information in the special cases just described, it is not generally applicable. For example, for pacemaker-dependent patients with complete heart block, adjusting the AV delay does not affect the QRS width in any meaningful way. Assessment of hemodynamic performance on a beat-to-beat basis would be a direct and general way to provide for the optimization of pace parameters. It would be operable both in the common applications of sinus node dysfunction and heart block, as well as the special cases of biventricular pacing in heart failure and dual chamber pacing in hypertrophic obstructive cardiomyopathy. Indeed, the information it provides would be interpreted the same way whether the goal of therapy is to improve ventricular synchrony, as is the case with dilated cardiomyopathy, or to decrease synchrony, as with hypertrophic obstructive cardiomyopathy.

In U.S. Pat. No. 5,554,177, Kieval and Soykan present a pace-parameter optimization system that uses heart sounds as the feedback variable. They note that an acoustic sensor does not necessarily require intracardiac placement, but instead can be placed in the housing of the implanted device. As discussed above, this is advantageous because it does not require costly lead modifications, nor does it impose restrictive device/lead compatibility constraints. In their disclosure, pace-parameter optimization is performed using as feedback a particular heart sound which is "an artifact indication of a less than optimal heart condition." Their disclosure isolates the sound in time and adjusts the pacing parameters in order to "lower the volume" of the sound. In the preferred embodiment the volume of the sound of mitral regurgitation is minimized. The generality of this approach is limited in several ways. Conditions that lack an artifact indication can not support this approach to parameter optimization. Furthermore, not all patients with a given disease, such as the example of dilated cardiomyopathy used by the authors to illustrate the invention, will have a given artifact indication, such as mitral regurgitation. More importantly, this approach, in which a particular abnormal heart sound is minimized, would fail dramatically in some applications of hemodynamic assessment, such as arrhythmia discrimination. Indeed, because it seeks to minimize heart sounds, the measure proposed in the '177 Patent would falsely classify a hemodynamically unstable rhythm, such as ventricular fibrillation, as hemodynamically stable. Even in application to the examples presented in the '177 Patent, hypertrophic and dilated cardiomyopathy, one is struck by the technical challenge of determining whether the minimization of the artifact heart sound results from, on the one hand, desirable parameter settings that increase cardiac hemodynamic performance, or, on the other hand, undesirable parameter settings that significantly compromise cardiac synchrony and therefore reduce the degree of regurgitation. The fundamental drawback of the approach the authors describe is that it does not provide hemodynamic sensing. What is reflected in the intensity of the sound of mitral regurgitation is the backward jet of blood into the left atrium from the left ventricle, not the forward output of blood from the heart. What is needed is a measure that is directly related to the hemodynamic function of the heart.

In U.S. Pat. No. 4,356,827, Uemura et al. describe the use of Korotkoff sounds in the detection of cardiac arrhythmias. Korotkoff sounds are the sounds generated when blood is pumped through an artery subjected to an external pressure which lies between the systolic and diastolic pressures. The invention clearly provides a measure of hemodynamic status in that it identifies the systolic and diastolic pressures as being respectively above and below the externally applied pressure. As a measure of hemodynamic status it is generally applicable to the problems presented above. However, the external pressure cuff precludes the use of the invention in an implanted device. A modified embodiment configured for internal use can be imagined, but such an approach would require surgical dissection of an artery and attachment of a pressure cuff, or similar element. The pressure applied by the cuff could be dynamically changed when the arterial pressure is checked, for example, as when tachycardia is detected. However, this approach would clearly increase both the device cost and the difficulty and duration of the implant procedure. These considerations make the practicality of such an approach questionable.

Lekholm, in U.S. Pat. No. 4,763,646, describes identifying various portions of the cardiac cycle using heart sounds to provide timing information for a pacemaker. For example, heart sounds are used to provide detection of ventricular contraction in order to inhibit the delivery of a ventricular pace pulse in a DDD pacer. In addition, an application to arrhythmia discrimination is presented. Specifically, heart sounds are used to determine the heart rate, from which tachycardia is detected. In contrast, changes in amplitude and the frequency spectrum of the heart sounds are used for the detection of fibrillation. This approach in effect detects the reduced hemodynamic performance of the heart that results from ventricular fibrillation (VF). However, because of its rapidly lethal character, it is necessary to quickly terminate VF, regardless of the hemodynamic status of the patient early in the arrhythmia. In contrast to VF, it is in the region of rate overlap between ventricular and supraventricular tachycardias that a transducer which is sensitive to diminished hemodynamic status would be most useful. In this region, however, the invention presented in the '646 Patent uses heart sounds only to calculate rate, not to assess the hemodynamic performance of the heart. A final application of heart sounds in the '646 Patent is to capture verification. Other systems using heart sounds are described in U.S. Pat. Nos. 3,985,121, 5,685,317, and 5,687,738, though none of these make use of sounds in hemodynamic assessment.

Regarding the physical location of a sensor used by an implantable device, as described above in the context of pressure sensing in the right ventricle, it is desirable to place the sensor outside the bloodstream. Incorporation of the sensor inside or on the device would be most convenient. Prutchi and Paul, in U.S. Pat. No. 5,556,421 propose placement of a sensor within the header of a cardiac device. A disadvantage of this approach is that it does not necessarily provide for the optimal signal transduction of a particular sensor. For example, the performance of the optical sensor described in the Prutchi and Paul Patent would be so severely degraded by direct transmission of light from source to detector that one skilled in the art would question the functionality of the proposed solution. In addition, placement in a rigid epoxy header is simply not an option for some sensors, such as sound sensors, because of the dramatic degradation in the signal-to-noise ratio that the rigid header would impose. What is needed is a method of incorporating a hemodynamic sensor into a implantable device, providing it optimal access to the external milieu so that the signal of interest is optimally transduced, maintaining the hermetic enclosure provided by the device housing, and minimizing the added volume that the sensor imposes.

Fearnot in U.S. Pat. No. 5,040,533 teaches placement of a generalized window in the housing of the cardiac device. The window might be transparent to facilitate the transmission of light or flexible to facilitate pressure transduction. While the convenience, from the clinician's perspective, of incorporating the sensors into the housing of the cardiac device is an obvious advantage, the technical difficulty in maintaining a hermetic seal between two different materials, particularly in a chronically implanted device, is equally obvious to one skilled in the art. The technical challenge is made more difficult by the greatly increased circumference, relative to that of standard feed-through connections known in the art, of the boundary between the window and the device housing. What is needed, therefore, is a method of placing a hemodynamic sensor in or on the device without compromising the integrity of the hermetic enclosure.

Because of the considerations described above, the principal object of the present invention is to provide an extravascular sensor that monitors a patient's hemodynamic status.

An additional goal of the present invention is to provide hemodynamic sensing over short time scales, i.e., on the time scale of a single cardiac beat.

Another object of the invention is to provide a means of determining whether electrical therapy is needed based on the hemodynamic status of the cardiac rhythm.

A further object is to provide a means of capture verification for cardiac pacemakers.

Still another object is to allow the optimization of the sensitivity of sensing circuitry.

Yet another object is to provide immunity from electrical noise in the sensing of cardiac activity.

An additional object of the invention is to provide hemodynamic sensing for the optimization of pacing parameters.

Still another object of the invention is to provide for extravascular placement of the device and sensors, which minimizes the perioperative and long-term risk of complications.

Further objects and advantages will become apparent from a consideration of the ensuing description and drawings.

BRIEF SUMMARY OF THE INVENTION

The present invention is directed to an implantable medical device such as a pacemaker or implantable cardioverter defibrillator or stand-alone hemodynamic monitor that uses an acoustic transducer responsive to heart sounds to detect the hemodynamic status of a patient. A hermetic housing such as a titanium "can" encloses the device electronics and the device housing includes at least one substantially planar face configured to act as a diaphragm in response to acoustic waves. A transducer positioned inside the device housing provides an output signal to the device electronics responsive to vibration of the diaphragm.

In a first embodiment of the invention, the transducer is a piezoelectric element positioned on the diaphragm. In a second embodiment, the transducer comprises a laser interferometry source and detector having a laser light reflecting off of the diaphragm.

The sensed heart sounds signals may be used to discriminate among possible cardiac arrhythmias, particularly hemodynamically stable and unstable arrhythmias such as may be the case between an atrial tachycardia and a ventricular tachycardia.

The medical device of the invention may further include an accelerometer for detecting motion artifacts that could interfere with the sensed heart sounds signals.

In another embodiment the medical device of the invention is implemented in an implantable pulse generator that provides pacing therapy to a patient's heart. The electronic circuitry uses the sensed heart sounds signals to optimize the timing of pacing pulses provided to said patient's heart. This may include a posture sensor that triggers optimization of the timing of pacing pulses upon sensing of a change of the patient's posture. The voltage level of pacing pulses provided to said patient's heart may also be optimized or pacing capture may be verified. In addition, the sensed heart sounds signals may be used to optimize electrical sensing of cardiac signals.

BRIEF DESCRIPTION OF THE SEVERAL VIEWS OF THE DRAWINGS

FIGS. 3a–3e provide top sectional views of the preferred and alternate embodiments of the sound sensor;

DETAILED DESCRIPTION OF THE INVENTION

Figure 1:
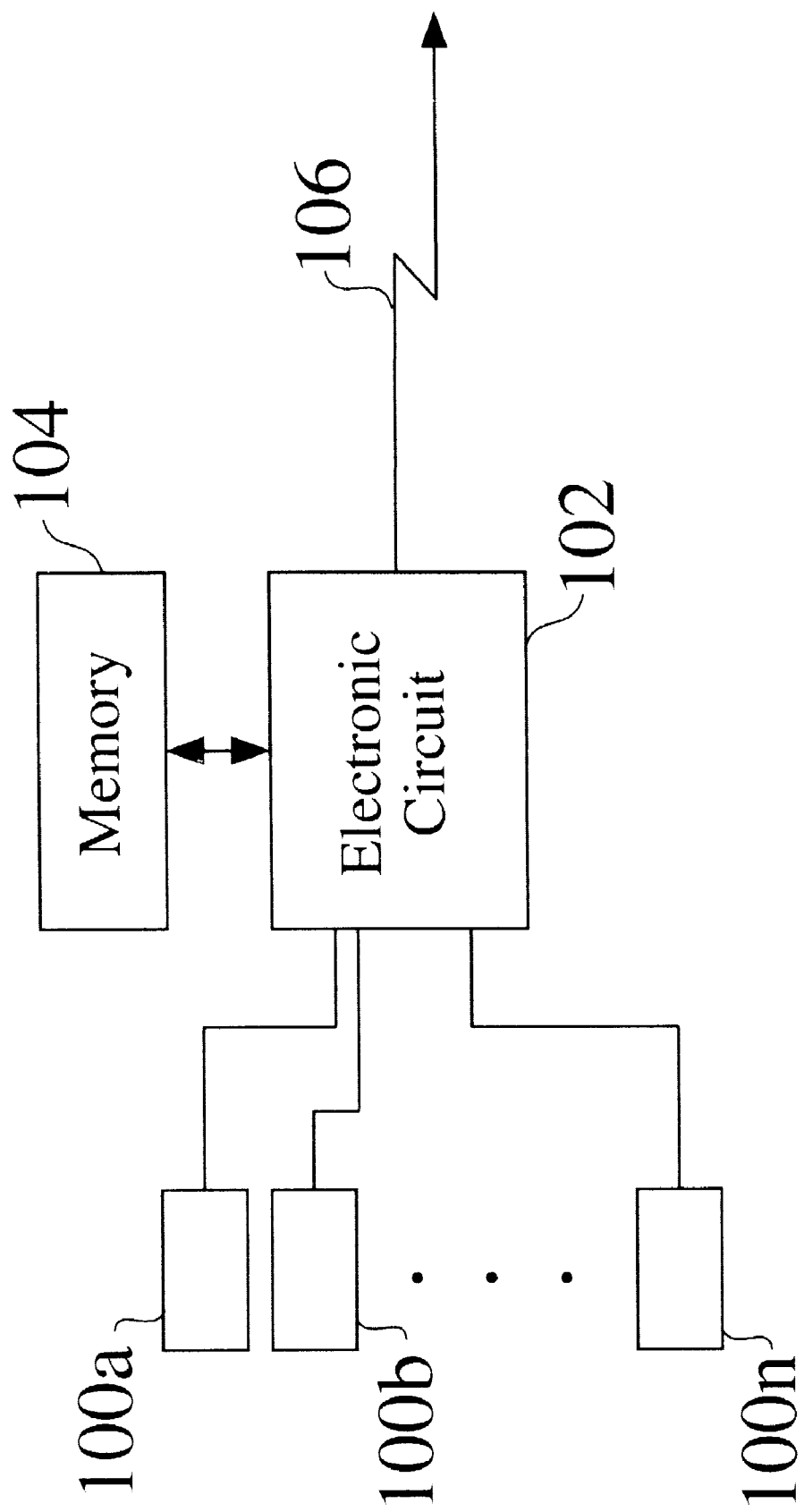
FIG. 1 shows a functional block diagram of a preferred embodiment of the invention.

A functional block diagram of hemodynamic sensors incorporated into an implantable device is shown in FIG. 1. One or a plurality of sensors 100a, 100b, . . . 100n is connected to an electronic circuit 102. When the implantable device is a pacemaker or ICD, the electronic circuit 102 is further connected to a cardiac lead 106, capable of delivering pace stimuli or antitachycardia therapy to the heart. The diagrammatic representation of sensors 100a, . . . , 100n and lead 106 illustrates the functional distinction, but does not imply a separate physical embodiment. The device includes a memory 104 and electronic circuit 102 that contains a low-power microprocessor.

In alternate embodiments the microprocessor is excluded and control functions are hard-wired, or control and higher level processing is performed by a microcontroller, an embedded system, a programmable logic device such as a field-programmable logic array, or a combinatorial implementation of a state machine.

In other alternate embodiments a memory is not included in the implantable device, rather, data is continuously telemetered to an external module which provides analysis or storage.

The lead 106 might not be included in some implantable devices, such as an extravascular monitor.

The configuration illustrated in FIG. 1 can also apply to external devices which use hemodynamic sensors, such as external defibrillators, pacemakers and patient monitors.

Figure 2:
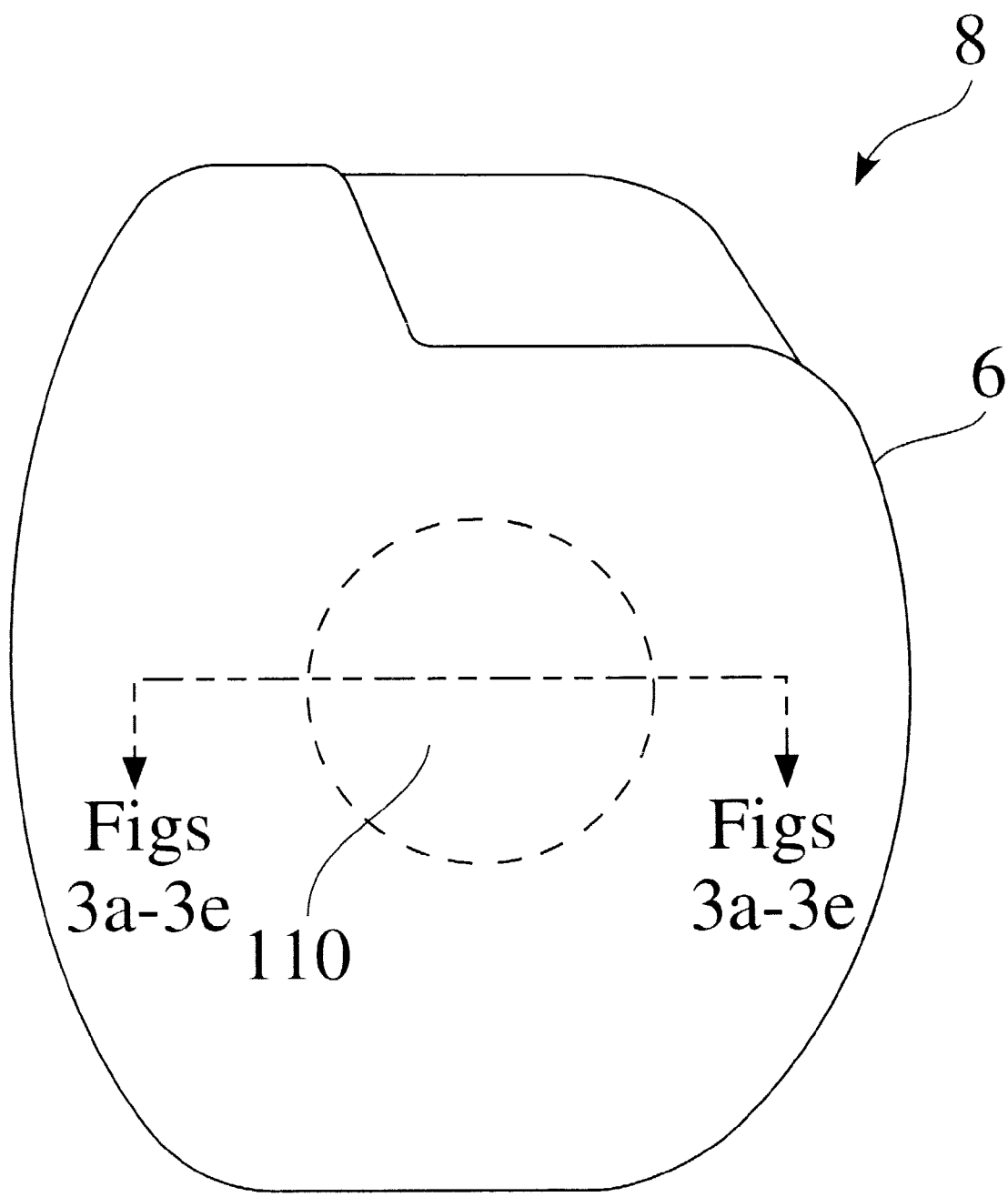
FIG. 2 provides an external view of the preferred embodiment of the sound sensor.

An extravascular hemodynamic sensor is provided which uses acoustic information originating from the heart. As illustrated in FIG. 2, the housing 6 of an implantable device 8 serves as an acoustic diaphragm 110, whose location is indicated by the dotted line. The microphone diaphragm is preferably placed on the side of the device 8 which faces the interior of the body after implant.

FIGS. 3a–3e show the cross section of a portion of the monitor housing that includes the microphone diaphragm 110 and mechanical-to-electrical transducer 116. In the preferred embodiment of the acoustic sensor, illustrated in FIG. 3a, the unmodified face of the device housing 6 serves as the acoustic diaphragm. A mechanical to electrical transducer 116, preferably a piezoelectric element such as that provided by MSI (Measurement Specialties, Inc, Sensor Products Division, Folsom, Calif.), is attached near the middle of diaphragm. A pair of leads 118 of the transducer 116 is connected to the inputs of a signal conditioning circuit (not shown), which is contained in the electronic circuit 102 shown in FIG. 1. The signal conditioning, filtering, and amplification appropriate for a piezoelectric sound transducer is well known in the field of sensors, and is therefore not presented here. Using the unmodified device housing is desirable because no special manufacturing steps or modifications to the conventional device housing are required. This approach is satisfactory if the lowest resonant frequency of the unmodified housing is above the frequency range of interest, which is 5–300 Hz for hemodynamic sensing, and the vibrational modes that are excited with stimulus frequencies in the range of interest do not generate nodes at the location where the transducer 116 is placed. The transducer 116 is preferably centered on the location of the device housing 6 that experiences a vibrational maximum when stimulated acoustically.

Figure 4A:
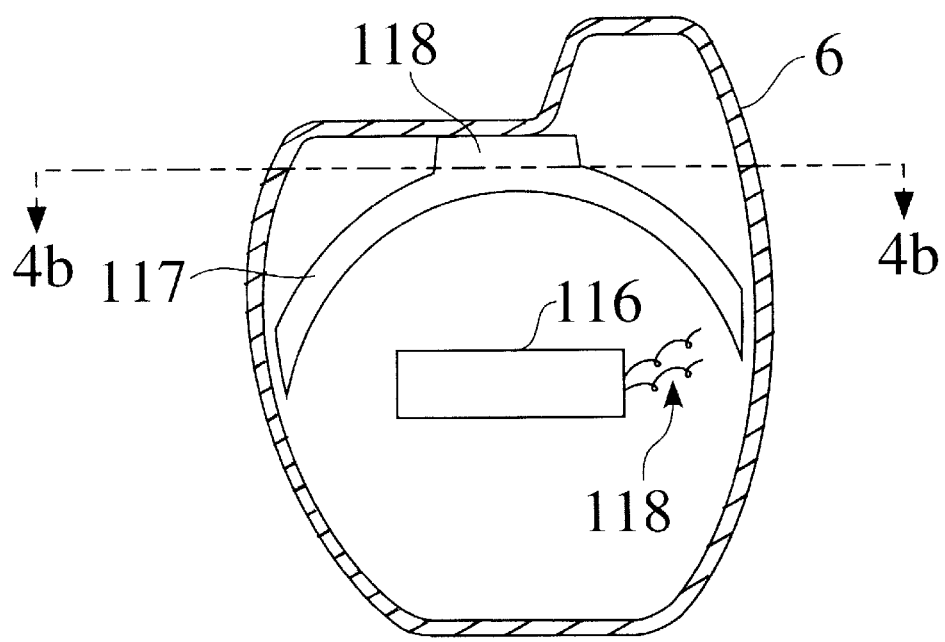
FIGS. 4a–4b provide various views of an alternate embodiment of the sound sensor.

An alternate embodiment of the acoustic sensor is illustrated in FIG. 4a, which shows the interior view of the device housing 6 with mechanical-to-electrical transducer 116 placed in the center of the device. In this alternate embodiment a strut 117 is resistance welded to the inside of the housing 6. This establishes a mechanically better defined diaphragm than the unmodified housing, at the cost of extra material, weight, volume and an extra manufacturing step. By reducing the effective area of the diaphragm the strut increases its resonant frequency, and reduces the number of vibrational nodes by providing a nearly circular geometry.

Figure 4B:
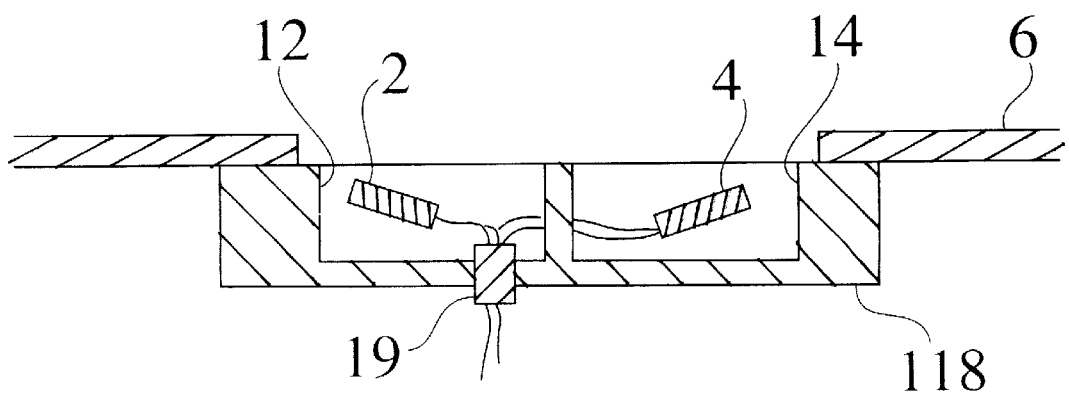

The strut 117 can be manufactured with a pocket or pockets to accommodate additional transducers, as illustrated in the cross section shown in FIG. 4b. An optical source 2 and detector 4 are placed in separate pockets or recesses 12 and 14, respectively. The hermetic enclosure of the device is maintained by connecting source 2 and detector 4 to internal circuitry using a feed-through connector 19, and by laser-welding the junction between the strut 118 and the device housing 6.

In another alternate embodiment illustrated in FIG. 3, a mechanically well-defined diaphragm 110 is created during the same manufacturing step in which the device housing 6 is formed. This is achieved by including concentric ridges and grooves in the die such that the illustrated pattern results. The resulting ridges and groves in the formed device housing 6 produce a well-defined diaphragm 110 that vibrates according to the pressure wave of the incident sound, with greatest amplitude of oscillation at the diaphragm center. In addition to the ease of manufacturing that this embodiment offers, it is desirable because the preferred thickness of the diaphragm 110 is 0.005–0.015 inches, which is the typical wall thickness used in conventional implantable devices such as pacemakers and defibrillators. In an alternate manufacturing process, the ridges and grooves which define the diaphragm can be formed, coined, or machined in a separate step after the housing is formed or produced. Other arrangements of groves and ridges are possible. In still another embodiment no grove is produced on the exterior of the housing. While this compromises the mechanical definition of the diaphragm, it provides a smooth exterior surface which minimizes the risk of infection.

Figure 3C:
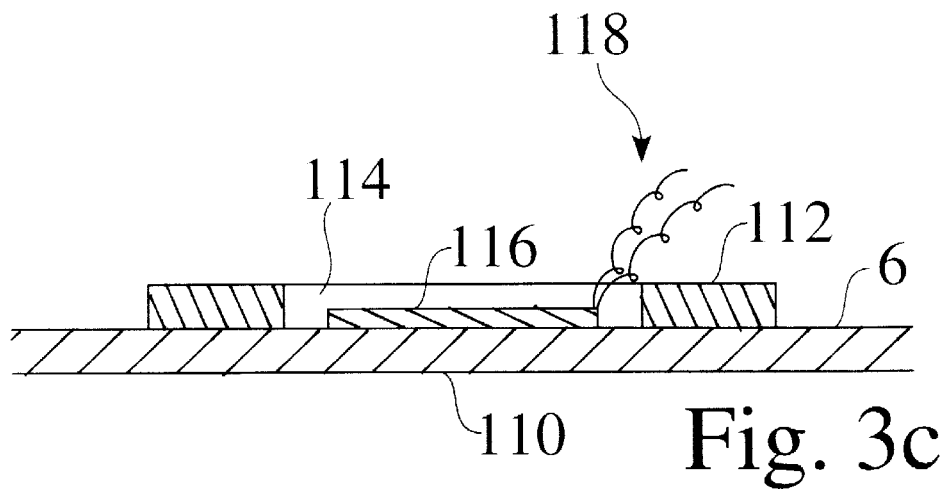

In still another alternate embodiment illustrated in FIG. 3c, an annular disk or plate 112 with a circular hole 114 is attached to the inside of the monitor housing 6 using a laser weld, a thermal weld, glue, epoxy, or some other suitable attachment means. The annular disk or plate 112 can be a functional component of the monitor, such as a battery, capacitor, or circuit board. Because of the encircling rigid and relatively more massive annular disk or plate 112, the portion of monitor housing 6 that is exposed through the circular hole 114 is a mechanically well-defined diaphragm 110. When sound strikes the device housing 6, the diaphragm 110 moves according to the pressure wave of the sound, with the greatest movement amplitude occurring at the center of the diaphragm.

Figure 3D:
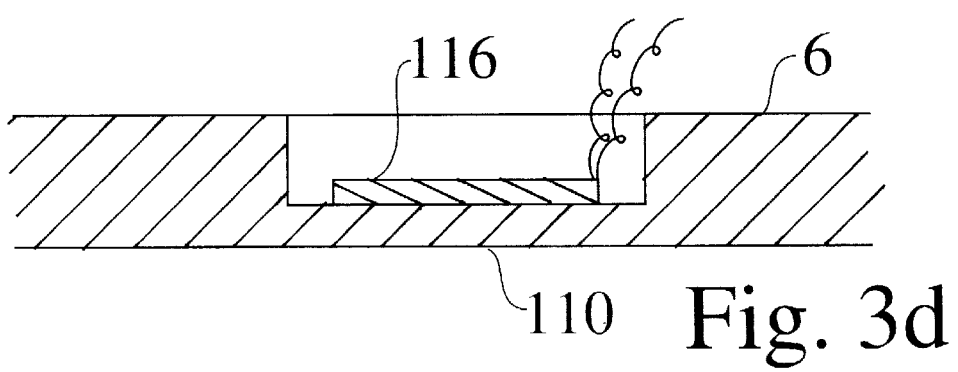

FIG. 3d shows yet another alternate embodiment of the sound sensor. Here the device housing 6 is formed, stamped, or machined such that the diaphragm thickness, typically 0.005 inches, is less than the thickness of the surrounding housing. This provides a mechanically well-defined diaphragm 110 which, when sound strikes the device, undergoes the largest amplitude deflection at its center. Transducer 116 is used to sense vibrational motion of diaphragm 110.

Figure 3E:
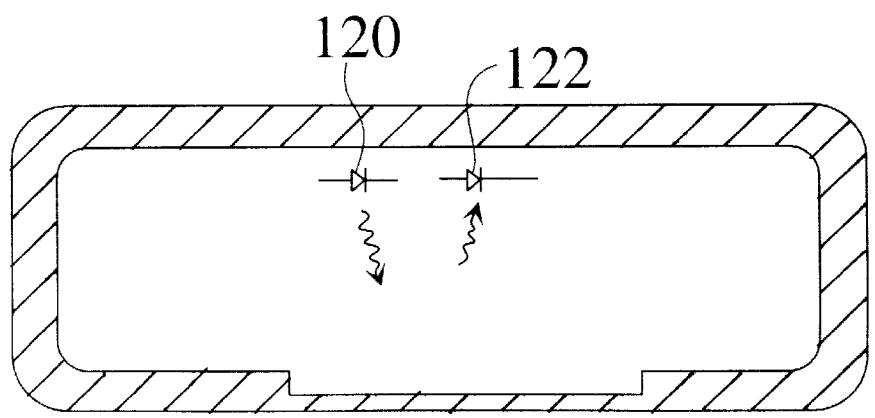

FIG. 3e shows an alternate embodiment of the mechanical-to-electrical transducer, in which a laser diode 120 and photodetector 122, such as a phototransistor, photodiode, piezoelectric, or thermoelectric material such as PVDF, are configured so that transduction is performed by laser interferometery. The technology of focusing elements and the related circuitry, not shown, are well developed in the art of interferometery, as discussed in the book "Handbook of Modem Sensors," by Jacob Fraden.

Still other embodiments of the acoustic sensor include microphone, accelerometer, and pressure transducer. Implementations include capacitive, inductive, and resistive transduction. Both macroscopic and microscopic transduction elements, as with microelectromechanical systems, can be used.

Figure 5:
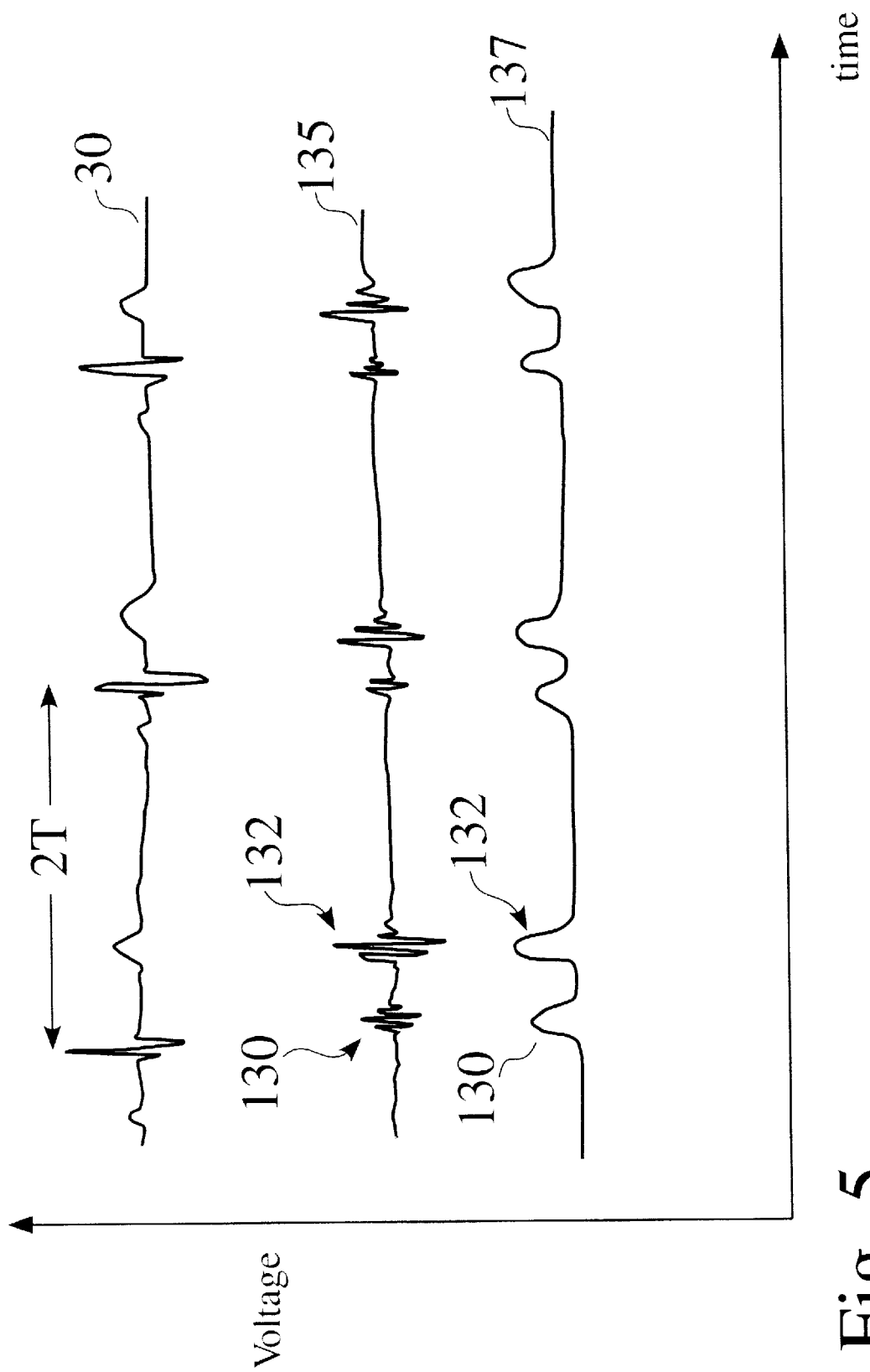
FIG. 5 illustrates the time tracing of the ECG and sound signal.

A typical waveform generated by the acoustic sensor circuit is illustrated in FIG. 5. For timing reference, the ECG signal 30 is illustrated. Both the wide-band phonocardiogram 135 and the rectified and low-pass filtered phonocardiogram 137 are shown. A few milliseconds to a few tens of milliseconds after the QRS complex, the tricuspid and mitral valves close, creating the first heart sound 130, referred to as 'S1' in clinical settings. During or near the T wave the aortic and pulmonic valves close, producing the second heart sound 132, referred to as 'S2' in clinical settings. The intensity of these sounds is related to the pressure gradients that are generated across the valves. Thus, during hemodynamically stable rhythms, such as sinus tachycardia and typical low-rate episodes atrial fibrillation in patients with normal ventricular function, the amplitude, energy, and intensity of S1 and S2 will be greater than during hemodynamically unstable rhythms, such as ventricular fibrillation, some ventricular tachycardias, and some supraventricular tachycardias. Similarly, pacing parameters which result in more efficient mechanical pumping will produce sounds of greater intensity. Measures of the intensity, such as amplitude, energy, rectified low-pass signal, and integrated rectified signal, can therefore be used as a surrogate for pulse amplitude.

FIG. 5 illustrates the appearance of the acoustic waveform during sinus rhythm. During hemodynamically unstable rhythms, the amplitude of the heart sound is greatly diminished or nonexistent. Also, the beat-to-beat amplitude that is recorded may vary depending on the underlying rhythm. For example, in VT the heart sounds should be rapid, regularly spaced, and of approximately the same amplitude. The amplitude will be small or nonexistent in hemodynamically unstable episodes of VT, but will remain near-normal during hemodynamically stable VT. In contrast, during AF which is conducted to the ventricles, the heart sound amplitudes will be irregularly spaced, and of variable amplitude since the degree of ventricular preload can vary considerably from beat to beat, though more hemodynamically stable episodes of the arrhythmia will have a larger average pulse amplitude than less stable episodes.

Because of the significant difference in acoustic impedance between tissue and air, most of the acoustic energy that is incident on the body from the air is reflected back into the air, so that minimal interference will occur from external sound sources. However, internal sources of sound, such as voice and bowel sounds, will be readily detected by the acoustic sensor. To minimize noise artifact, from both internal and external sources, it is desirable to use filtering so that the frequency range of heart sounds, roughly 5–300 Hz, is preserved, while the energy of noise sources such as voice is minimized.

Figure 6:
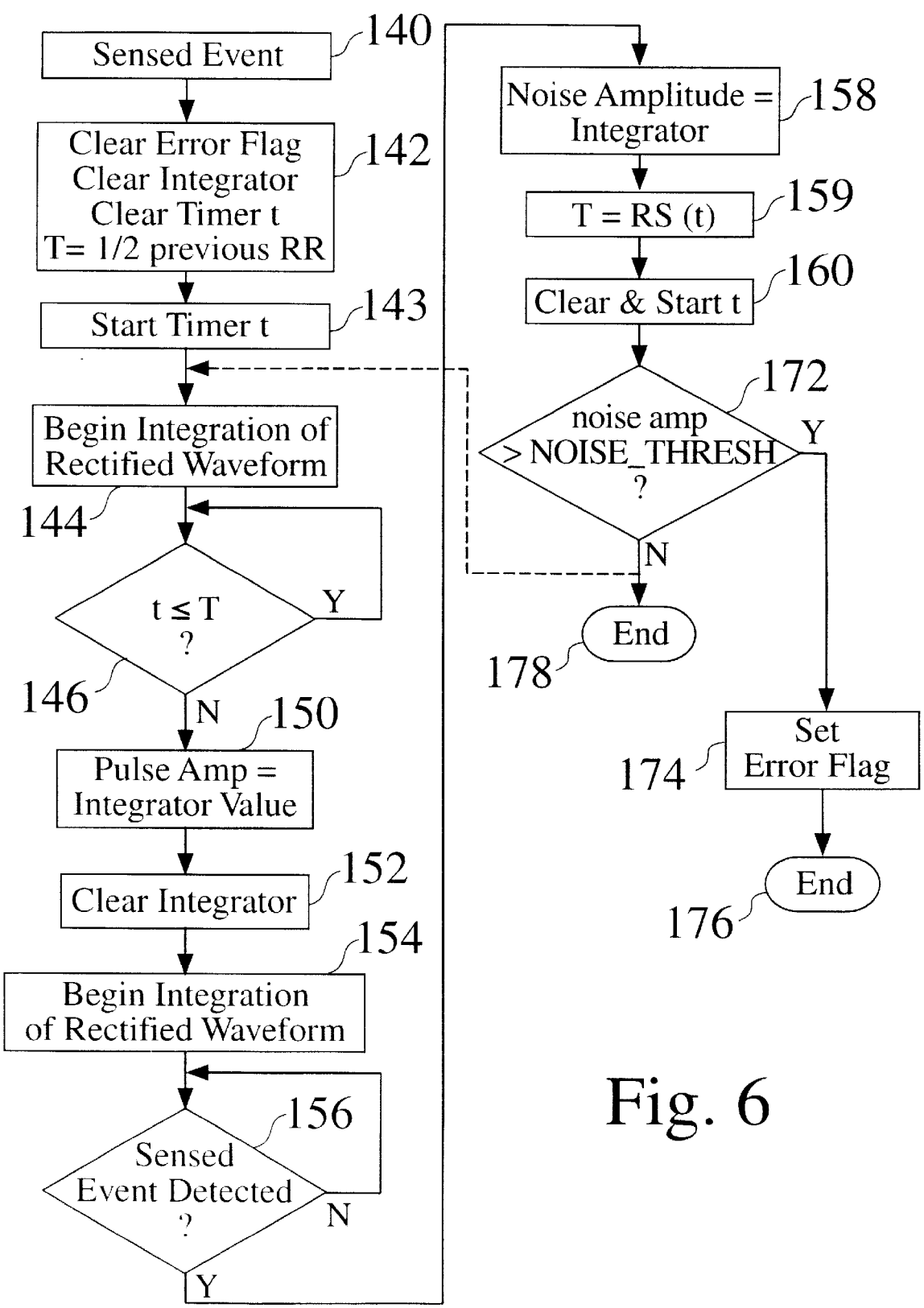
FIG. 6 is a flowchart which describes the processing performed by the electronic circuit on the output of the sound sensor.

The preferred embodiment of the algorithm for pulse amplitude measurement using an acoustic sensor is presented in FIG. 6. In this embodiment both pulse amplitude measurement and artifact detection are performed. Other embodiments of pulse measurement with or without artifact detection are obviously possible. In the preferred embodiment the algorithm begins with the detection of a sensed event at step 140. The sensed event is preferably a QRS complex, but can be any other marker of atrial or ventricular depolarization, or electrical activity that is interpreted as such by the device. In the initialization step 142, an error flag is cleared, a time variable t is set to zero, and an integrator is set to zero. In addition, the variable T is set to one-half the duration of the previous cardiac cycle, defined as the time between two successive sensed events. The integrator is preferably implemented in analog hardware, while the error flag and time variable are implemented digitally, though other embodiments exist. The time t is represented by the contents of a register, which, as is described below, is incremented until a rate-dependent time has elapsed. After the initialization step 142 the timer t is started at step 143 and the analog integrator begins integrating a rectified version of the acoustic waveform signal at 144. At step 146, the time t is tested against a the interval T. Integration continues until the test is negative, i.e., until the interval T has elapsed, at which point the analog voltage of the integrator is converted to a digital representation and stored as the pulse amplitude for later analysis, step 150. The integrator is again cleared, at step 152, and integration of the rectified analog waveform of the acoustic signal again commences at step 154. Integration continues until the next sensed event is detected, step 156, at which point the contents of the timer t represents the duration of the just-completed cardiac cycle. At step 158 the analog voltage of the integrator is converted to a digital representation of the noise level and stored as the noise amplitude for later analysis. The contents of the timer t is divided by two using a right shift at step 159, and is assigned to the variable T in preparation for the next iteration of the algorithm. The timer t is cleared and restarted at step 160. The normalized noise amplitude obtained in step 158 is compared to a predetermined noise threshold, NOISE_THRESH at step 172. If greater than the threshold, an error flag is set, step 174, and the algorithm terminates, step 176. If the noise amplitude is less than the threshold then the pulse amplitude calculated at step 150 is considered valid, and indicated as such by the error flag, which remains cleared. Thus, a valid pulse amplitude is available in memory for use by other algorithms. The present algorithm then terminates at step 178, alternatively, it can repeat by reentering the flowchart above step 144, as indicated by the dotted line.

Alternate embodiments include different methods of making the integration windows rate-dependent. For example, with dual-chamber devices, which have sensing electrodes in both the atrium and the ventricle, or other devices which can detect atrial depolarization, the atrial depolarization is used to initiate the beginning of a noise-checking window, while the ventricular depolarization (QRS complex) defines the end of it. Because in this embodiment the noise-checking window precedes the ventricular depolarization of interest, the validity of the calculated pulse amplitude will be known as soon as the pulse amplitude calculation is complete.

In the preferred embodiment of the pulse amplitude calculation for the acoustic sensor, the unnormalized value is used under the premise that the variation in the integrated signal due to rate-dependent changes in the window length is small enough that it will not mask the differences that result in the presence and absence of noise. In other embodiments the integrated results are normalized by the length of the rate-dependent integration windows. In still other embodiments the integration windows are of fixed duration, so that normalization is not necessary.

In another alternate embodiment systolic pulses are detected using a template matching algorithm, such as cross correlation or some other correlation measure. An excursion of the sound signal beyond a predetermined threshold above baseline initiates the calculation of the cross correlation function between the stored sound template for a systolic pulse and the current waveform. If the correlation is not sufficiently large, then noise is deemed to be responsible for the excursion and the hemodynamic sensor output is invalidated.

In still another alternate embodiment, detection of a systolic contraction using heart sounds and the detection of noise are performed in analog circuitry. The crossing of a threshold, predetermined to be lower than a hemodynamically stable systolic pulse but significantly higher than the noise floor, is detected in analog circuitry using a comparator. The threshold crossing causes the contents of a free-running timer to be copied to a register which contains the history of intervals between detected pulses. This information can be used alone or in conjunction with sensed electrical activity to determined whether an arrhythmia is present which requires electrical therapy. It can also be used to optimize electrical sensing threshold and gain settings and verify that a previously delivered pacing pulse successfully captured the myocardium. Since this approach does not retain the strength of the systolic contraction it cannot be used for pace parameter optimization.

In yet another alternate embodiment, a peak detector is used in analog circuitry to capture the maximum and/or minimum excursion of the pulse waveform. The waveform may first be rectified, followed by low-pass filtering and/or rectification. An electrical marker such as QRS complex or delivered pace pulse can be used to reset the peak detector at the beginning of each cardiac cycle.

The preferred embodiment of the algorithm which uses pulse amplitude for arrhythmia discrimination operates on a value of pulse amplitude, which can be obtained in any of a variety of ways. In particular, heart sounds can be used according to the algorithm described above in conjunction with FIG. 6 to obtain a measure of the strength of cardiac contraction. Other measures of hemodynamic function are possible, including ultrasound to detect changes in the diameter of the aorta or other vessels during the cardiac cycle, Doppler ultrasound to detect the blood flow through the arteries, cardiac motion detected by an accelerometer, ventricular volume detected by intracardiac or extracardiac impedance plethysmography, ventricular pressure determined by an intracavitary pressure transducer, and mechanical distention of the arteries measured, for example, using a strain gauge, accelerometer, or pressure transducer. The term 'pulse amplitude' is thus intended to be used in the generic sense as some measure of mechanical pumping efficacy of the heart, and is by no means intended to be interpreted solely as the literal physical distension of an artery. It is used to refer to any measure of mechanical cardiac hemodynamic function generated on a beat-by-beat basis.

Figure 7:
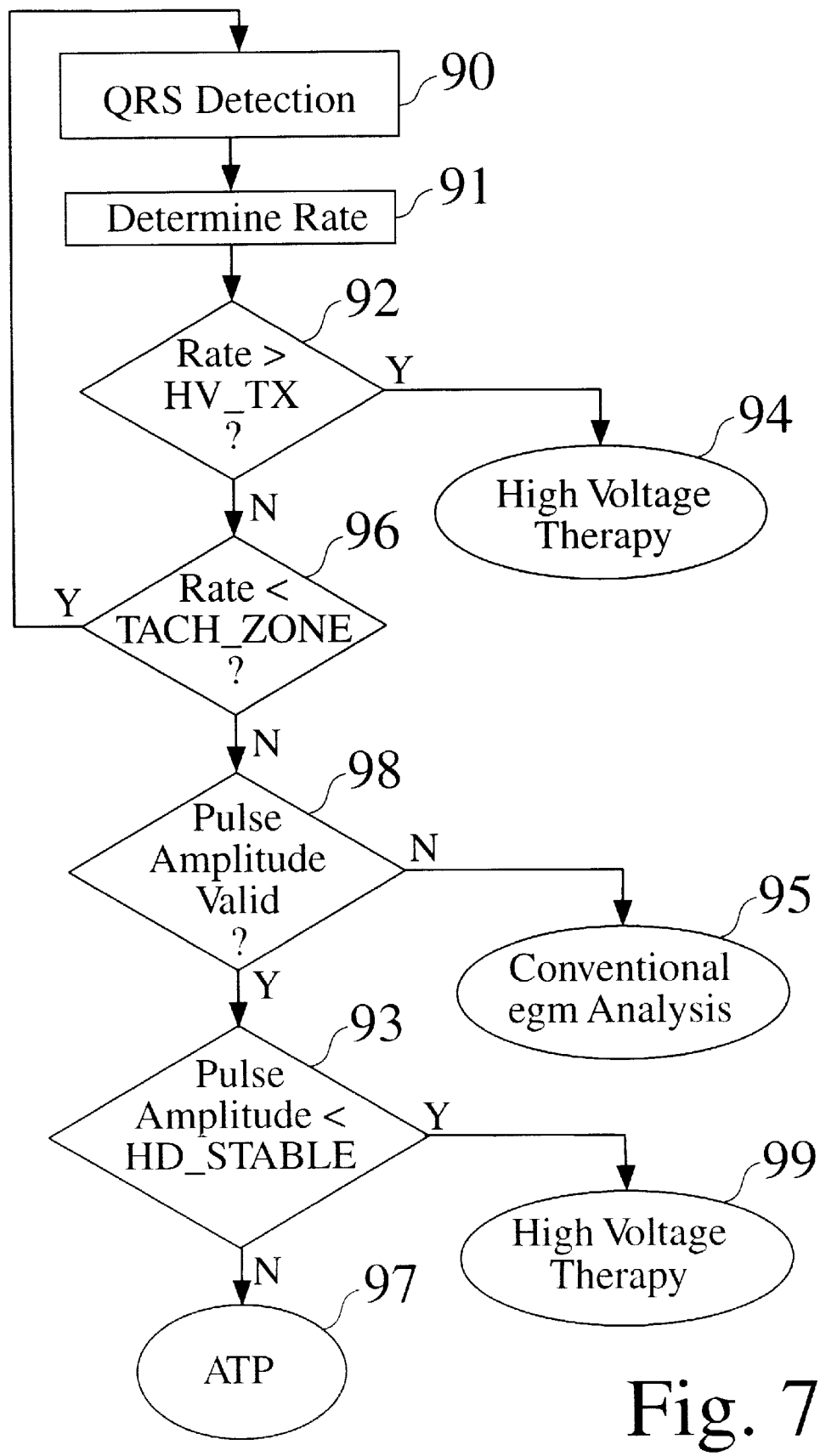
FIG. 7 is a flowchart which describes the processing performed by the electronic circuit on a generic pulse amplitude signal to provide arrhythmia discrimination.

The algorithm which performs tachyarrhythmia discrimination using hemodynamic sensing is presented in FIG. 7. After the detection of a sensed event, such as a ventricular depolarization, at step 90, the current heart rate is determined at step 91. If the rate is above a predetermined threshold for high voltage therapy, HV_TX, tested at step 92, then control is transferred to a conventional algorithm which immediately delivers high voltage therapy, step 94. Otherwise, the rate is compared to TACH_ZONE, which defines the low end of the tachycardia rate zone, at step 96. If the rate is below this threshold then control returns to step 90, and the algorithm awaits the detection of the next sensed event.

Otherwise, the rate is in the overlap zone. The algorithm therefore delivers therapy based on the hemodynamic status of the patient. The validity of the pulse amplitude, determined in the preferred embodiment of the pulse amplitude algorithm, such as those described above in conjunction with FIG. 6, is first tested at step 98. This test uses the error flag which is set in the preferred embodiment of the pulse amplitude algorithm when significant artifact is present in the underlying signal. If the pulse amplitude is invalid, then control passes to an algorithm that performs conventional electrogram analysis, step 95. If the value is valid, then it is tested against a predetermined threshold for hemodynamic stability at step 93. If the pulse amplitude is less than this value, then the high ventricular rate has compromised the hemodynamic stability of the patient to a degree that warrants high voltage therapy, regardless of the precise nature of the arrhythmia. This is delivered by passing control to a conventional high voltage therapy algorithm at step 99. On the other hand, if the pulse amplitude exceeds the threshold, the patient is maintaining sufficient hemodynamic stability to attempt low voltage therapy. Control therefore passes to a conventional anti-tachycardia pacing algorithm at step 97.

Rate and pulse amplitude are used in the preferred embodiment to determine what therapy is appropriate. Only if noise or motion artifact has rendered the pulse amplitude measure invalid is conventional electrogram analysis used. This is advantageous in that it greatly simplifies the design and development of the ICD and simplifies its operation from the point of view of the physician. In alternate embodiments conventional electrogram analysis is performed with the output of the hemodynamic sensor serving as a therapy accelerator, so that if a hemodynamically unstable rhythm is detected, more aggressive therapy is used.

In still other alternate embodiments the analysis examines the pattern of pulse amplitudes to identify the nature of the arrhythmia. For example, the detection of pulse amplitudes that vary on a beat-to-beat basis suggests that conducted AF is present. Similarly, other analysis using the pulse amplitude signal can better identify the nature of the underlying rhythm. The pulse amplitude signal can of course be used alone or in conjunction with other hemodynamic or electrical signals, such as the intracardiac electrogram.

In still other embodiments the pulse amplitude is continuously monitored in analog circuitry, such that the absence of a hemodynamically stable pulse within a predetermined time period will cause anti-arrhythmia therapy to be delivered. This approach can be implemented by resetting a free running counter each time a hemodynamicaly stable pulse is detected. If the counter reaches the predetermined time out period then an interrupt is generated which initiates the anti-arrhythmia therapy.

In yet other alternate embodiments statistics of pulse amplitude, such as average and variability, are retained and analyzed to determine the urgency of anti-arrhythmia therapy.

Figure 8:
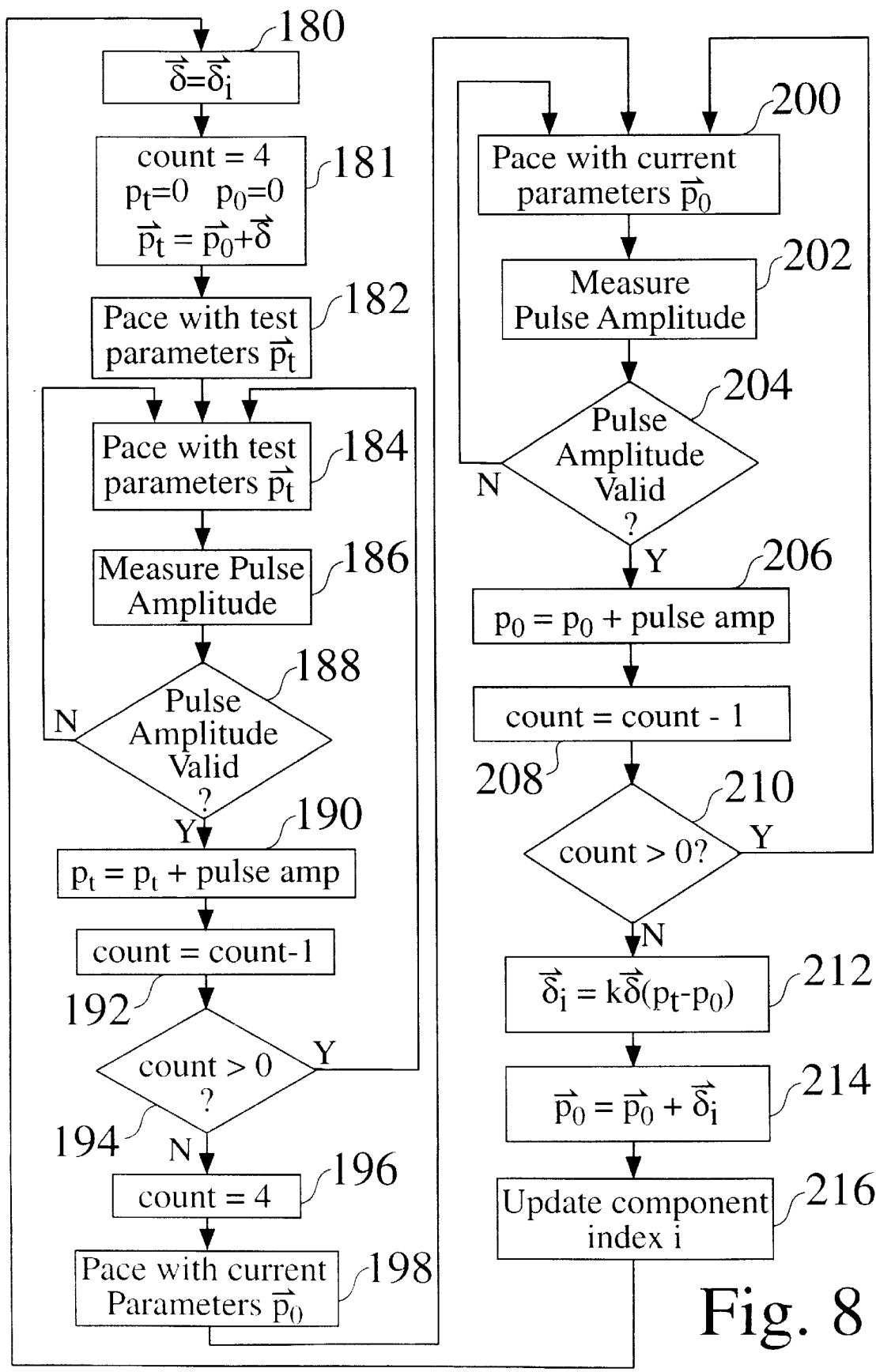
FIG. 8 is a flowchart which describes the processing performed by the electronic circuit on a generic pulse amplitude signal to provide pace-parameter optimization.

The preferred embodiment of the algorithm which performs pace-parameter optimization using a hemodynamic sensor is presented in FIG. 8. In this algorithm the pacing parameters are represented with a vector notion $\vec{p}$. In the preferred embodiment this vector represents the value of the RA-RV delay and the RV-LV delay, so that it has two components and optimization takes place over a two-dimensional space. The pacing rate is determined by a conventional rate-responsive pacing algorithm. The current set of pacing parameters is represented with the notation $\vec{p}_o$, and the set of test parameters is represented with the notation $\vec{p}_t$.

In $\vec{p}_o$ the preferred embodiment one component of the vector is modified, tested, and updated on each pass through the algorithm. For example, the current parameters might be $\vec{p}_o$=[100,30], where the first component represents the AV delay and the second component represents the RV-LV delay, both in msec. The test vector is $\vec{p}_t = \vec{p}_o + \vec{\delta}$, where $\vec{\delta}$=[10,0]. Thus the test parameters are identical to the current parameters but with an AV delay that is longer by 10 msec. The hemodynamic responses, $\vec{p}_t$ and $\vec{p}_o$, respectively, of $\vec{p}_t$ and $\vec{p}_o$ are obtained and $\vec{p}_o$ is updated depending on the responses.

Specifically, the component tested, in this example the AV delay, is changed by an amount proportional to the test difference and proportional to the difference between the hemodynamic responses, so that $\vec{p}_o \leftarrow \vec{p}_o + \kappa * \vec{\delta} * (p_t - p_o)$, where κ is a predetermined constant scale factor, $p_t$ represents the pulse amplitude associated with pacing using $\vec{p}_t$, $p_i$ is the pulse amplitude associated with pacing using $\vec{p}_o$, and ← denotes replacement. The amount by which $\vec{p}_o$ is updated is assigned to $\delta_i \delta_i = \kappa * \vec{\delta} * (p_t - p_o)$, and stored in memory for the next iteration that component i, the AV delay in this case, is updated.

Proceeding in detail through the preferred embodiment of the algorithm presented in FIG. 8, at step 180 the increment vector $\vec{\delta}$ is assigned the value $\vec{\delta}_i$, which is either the default increment setting or contains a value that was stored during a previous pass through the algorithm. The subscript i indicates that it is specific for the component presently being tested. At step 181 count is initialized to 4, and the variables $p_t$ and $p_o$, which represent the hemodynamic responses of the test and current parameter settings, respectively, are set to zero. In addition, the test parameter setting is assigned the value $\vec{p}_t = \vec{p}_o + \vec{\delta}$. A first pacing pulse is delivered using the test parameters $\vec{p}_t$ at step 182. The hemodynamic result of this pace set is not recorded since it is potentially influenced by preload conditions that are determined from the parameters that defined the previous paced beat. Another pace set is delivered at step 184 using $\vec{p}_t$. The pulse amplitude is determined at step 186 using the algorithms described above. A test for the validity of the pulse amplitude is made at step 188. If the pulse amplitude is not valid control returns to step 184 without the variables being modified. If the pulse amplitude is valid then $p_t$ is incremented by the measured pulse amplitude, step 190, and the count is decremented, step 192. If the count is greater than zero, step 194, control returns to step 184, otherwise, the count is set to 4 at step 196, and a first pace set is delivered using the current parameters $\vec{p}_o$ at step 198. Hemodynamic measurements are not made following this first beat because they could be influenced by preload conditions generated by the previous pace set, which used the test parameters $\vec{p}_t$. Another pace set is delivered using the current parameters $\vec{p}_o$ at step 200. Following this pace set the pulse amplitude is measured at step 202. If the pulse amplitude is not valid, tested at step 204, then control returns to step 200 without modification to the variables. If the pulse amplitude is valid, then $p_o$ is incremented by the pulse amplitude at step 206, and the count is decremented at step 208. Control returns to step 200 if the count is above zero at step 210, otherwise, the change to the current parameter set $\vec{\delta}_i$ is calculated at step 212 and used to update the current parameter set $\vec{p}_o$ at step 214. It is retained in memory for later use on successive passes through the algorithm. Finally, the component index i is updated at step 216, and control returns to step 180 for another pass through the algorithm.

This algorithm is advantageous in that the step size $\vec{\delta}_i$ is adaptive: it is largest in those regions of the optimization space that are far from the optimal parameter settings, where $p_o$ and $p_t$ are substantially different in magnitude, and it is smallest in those regions of the space that are close to the optimal settings, in which $p_o$ and $p_t$ are similar in magnitude so their difference is small. Thus the point representing the parameter settings speeds rapidly through the optimization space to the optimum. Furthermore, the trial step size $\vec{\delta}_i$ is taken to be the same as the last update. Both these attributes speed convergence to the optimal parameter settings and therefore allow rapid, dynamic adjustment of parameters, so that even changes in body position from supine to standing can be rapidly accommodated.

In the preferred embodiment the algorithm is run continuously. Alternate embodiments include performing the optimization intermittently, such as at periodic intervals or after a change of posture is detected by an accelerometer contained within the device. In still another alternate embodiment the scale factor k is slowly decreased so that the pacing parameters converge to a stable point. This embodiment is particularly useful for intermittent optimization.

In other alternate embodiments the newly updated pacing parameters are used to deliver some predetermined number of paced beats before a new parameter set is tested. This decreases the rate of convergence of the algorithm but allows the patient's hemodynamics to stabilize somewhat at the new pacing set.

Still other alternate embodiments optimize a different number of pacing parameters. For example, with atrial and single-chamber ventricular pacing, only the AV delay might be optimized. In this case $\vec{p}$ is a simple scalar. In another embodiment four-chamber pacing is used so that the RA-LA, RA-RV, and RA-LV intervals are optimized. In this case $\vec{p}$ is a three dimensional vector and optimization is performed over a three dimensional space.

In still other embodiments all components are tested and modified simultaneously, for example, using a simplex method.

Figure 9A:
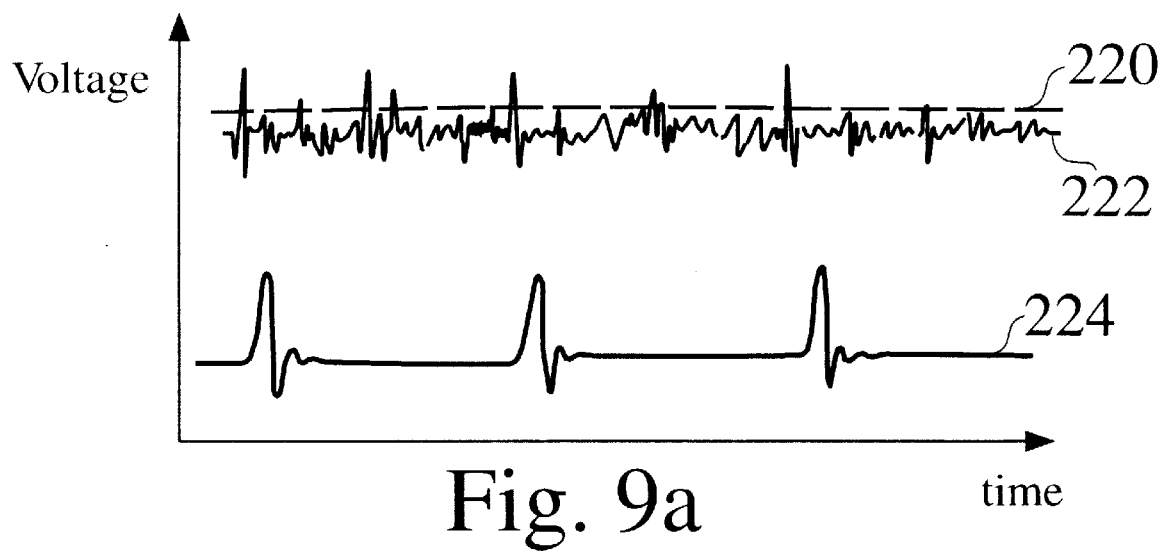
FIG. 9a–9b illustrate the time tracing of the electrogram and pulse amplitude signal during electrical over- and under-sensing.
Figure 9B:
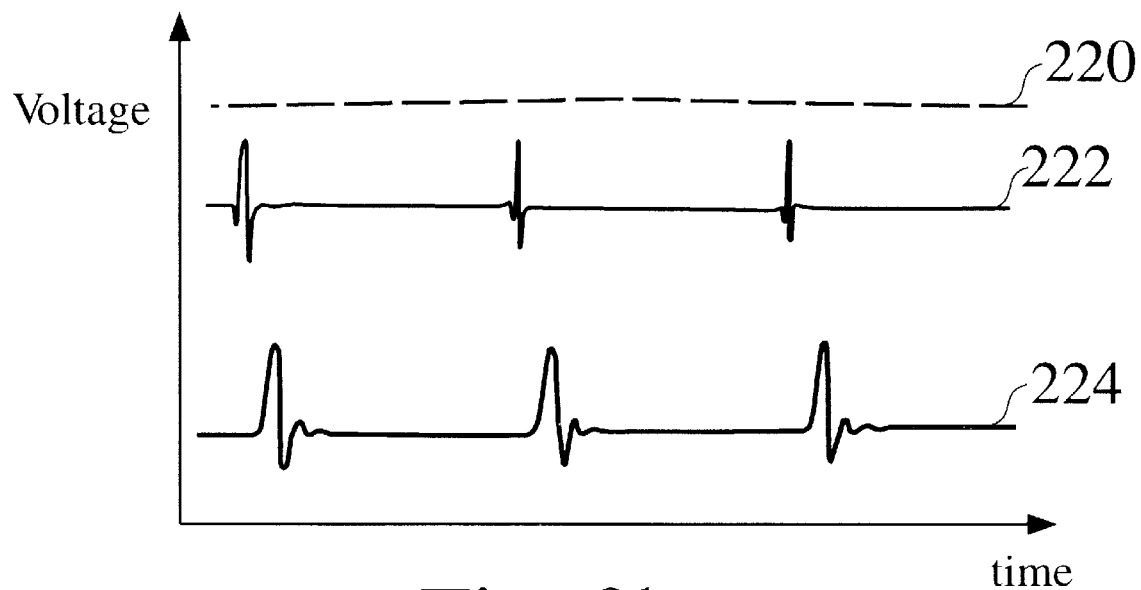

The problem of threshold or gain optimization for sensing of cardiac electrical activity is illustrated in FIGS. 9a and 9b. In FIG. 9a, the electrogram sensing threshold 220 is set too low so that the cardiac activity and the electrical noise that are present on the electrogram 222 cause the threshold 220 to be spuriously exceeded. The resulting oversensing may cause the device to mistakenly diagnose a tachy-arrhythmia and deliver unwarranted tachy-therapy. This not only hastens battery depletion, and is painful and distressing for the patient, but inappropriate tachy-therapy can itself be proarrhythmic. Since the hemodynamic sensor is immune to electrical noise, its signal 224 is clear and provides the basis for threshold optimization.

As illustrated in FIG. 9b, when the electrogram sensing threshold 220 is set too high, cardiac electrical activity on the electrogram 222 fails to exceed the threshold 220 and register a sensed event. In this case, undersensing may cause the device to mistakenly diagnose a brady-arrhythmia and deliver unwarranted brady-therapy. This is potentially dangerous because a pace-pulse delivered during cardiac repolarization can readily induce an arrhythmia. The hemodynamic sensor waveform 224 provides a basis for threshold optimization in this case as well. The signal 224 illustrated in FIGS. 9a and 9b can represent the output of the optical plethysmography sensor, the heart sound sensor, or some other sensor of cardiac hemodynamic function.

FIGS. 9a and 9b illustrate the problem of sensitivity optimization in terms of threshold settings. This formulation is obviously equivalent to gain adjustment in systems that use automatic gain control.

Figures 10A, 10B:
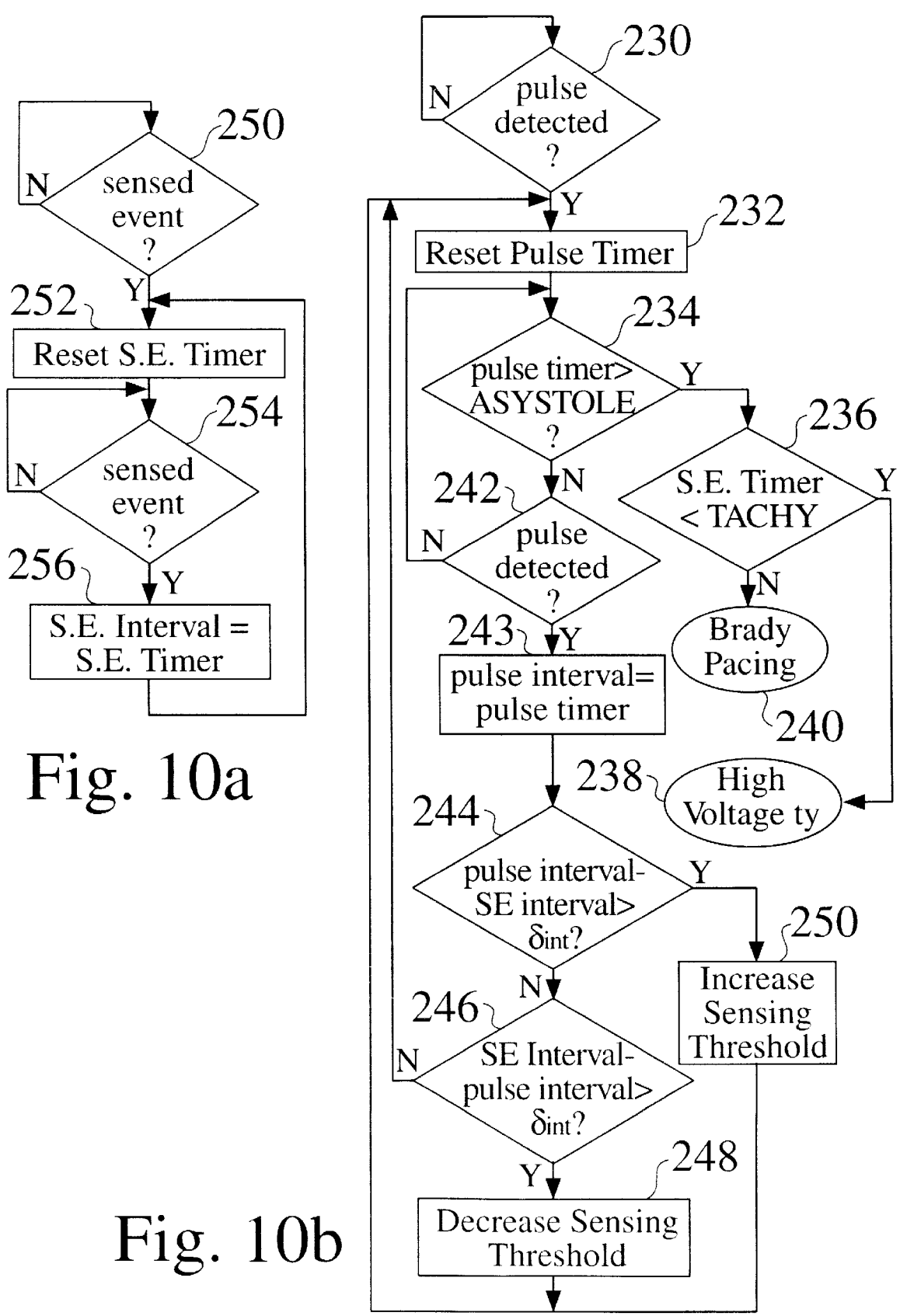
FIG. 10 is a flowchart which describes the processing performed by the electronic circuit on a generic pulse amplitude signal to provide optimization of sensing gain and threshold.

The threshold/gain optimization algorithm makes use of a record of intervals between systolic pulses and an independently obtained record of intervals between electrical sensed events. The algorithm by which the record of sensed events is obtained is illustrated in FIG. 10a. It is initialized with the first detection of an electrical sensed event at step 250. This causes the free-running sensed event timer to be reset at step 252. Upon detection of the next sensed event at step 254, the contents of the sensed event timer are transferred to the sensed event interval register at step 256, and control returns to step 252. As seen in FIG. 10b, independent of the execution of the algorithm that maintains the sensed event interval register, the algorithm that performs sensing threshold optimization begins with the first detection of a systolic pulse or cardiac contraction at step 230. The crossing of a threshold, predetermined to be much lower than the amplitude generated by a systolic contraction or pulse but much greater than baseline noise, is detected in analog circuitry using a comparator, which is recognized at step 230 as the detected pulse. The pulse detection causes the free-running pulse timer to be reset at step 232. At step 234, the pulse timer is compared against a predetermined duration ASYSTOLE, set to 1.5 seconds in the preferred embodiment. If the pulse timer exceeds this value then the most recent sensed event interval is compared at step 236 to a predetermined duration TACHY, set to 500 msec in the preferred embodiment. If the sensed event timer is less than TACHY then a hemodynamically unstable arrhythmia is diagnosed and control is transferred to the algorithm that delivers high voltage therapy at step 238. On the other hand, if the sensed event interval is greater than TACHY then a hemodynamically unstable bradycardia is diagnosed and control is transferred to the algorithm that delivers brady pacing therapy at step 240. Returning to step 234, if the pulse timer is less than ASYSTOLE, then a hemodynamically stable condition is diagnosed, and control is passed to step 242, where the detection of a pulse is tested. If no pulse is present then control returns to step 234. If a pulse was detected then the contents of the pulse timer is transferred to a pulse interval register at step 243. The difference between the just-obtained pulse interval and the most recent sensed event interval is compared to the predetermined value $\delta_{int}$ at step 244. Testing immediately after a systolic pulse is advantageous because, as illustrated in FIG. 9b, the most recently obtained electrical and hemodynamic intervals are derived from the same cardiac cycle. Because intrinsic variability is present, the intervals are not required to be equal at step 244, rather, the predetermined value $\delta_{int}$, preferably set to 75 msec, is used to account for this variability. If the test at step 244 is positive, so that the most recent hemodynamic interval exceeds the most recent electrical interval by more than $\delta_{int}$, then oversensing is deemed to be present in the electrical signal, and the electrical sensing threshold is increased at step 250, or alternatively, the electrical amplifier gain is decreased. If the test at step 244 is negative, then the difference between the most recent sensed event interval and the most recent pulse interval is compared to $\delta_{int}$. If the test is positive, then undersensing is deemed to be present, so the electrical sensing threshold is lowered at step 248, or, equivalently, the gain is increased. Control returns to step 232 after steps 248, 250, and a negative result at step 246.

More sophisticated alternate embodiments make use of interval histories, so that they are less sensitive to spurious events such as premature ventricular contractions and limited noise. Other embodiments perform optimization of hemodynamic sensing in addition to the optimization of electrical sensing. Still other embodiments identify noise or motion artifact on the hemodynamic signal using correlation analysis with a stored template, interval analysis, or frequency analysis.

Figure 11:
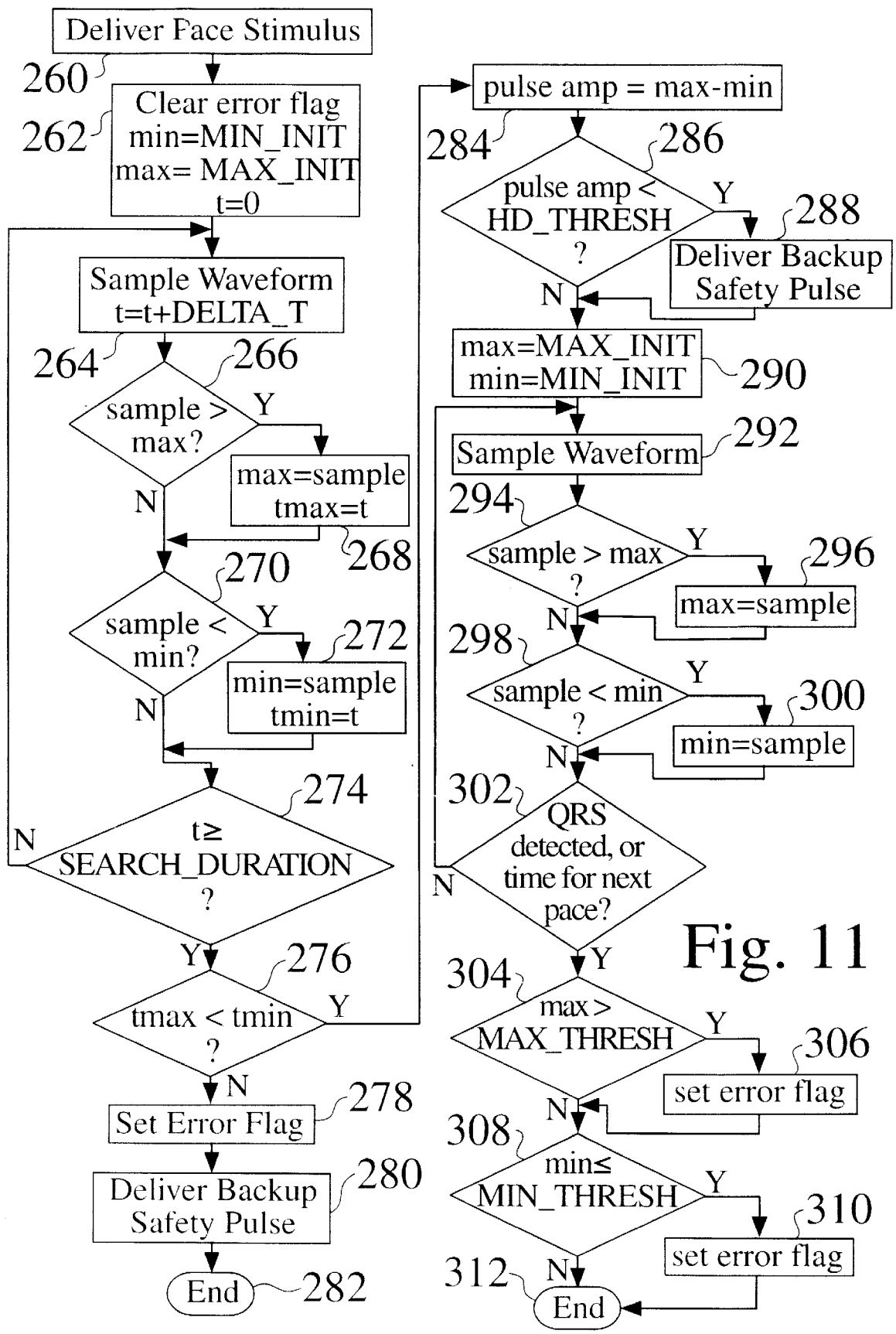
FIG. 11 is a flowchart which describes the processing performed by the electronic circuit on a generic pulse amplitude signal to provide capture verification.

The preferred embodiment of the algorithm that performs capture verification is presented in FIG. 11. The algorithm is used in conjunction with bradypacing or biventricular pacing, in which a low voltage stimulus is delivered to the ventricular myocardium to initiate a ventricular contraction. The algorithm verifies that a contraction was successfully induced by the pacing pulse by examining the hemodynamic response immediately after the pulse is delivered. To enhance safety, the algorithm also detects noise or motion artifact that might cause it to otherwise falsely conclude that a contraction had occurred.

The algorithm begins with the delivery of a pacing pulse at step 260. At step 262, an error flag is cleared, a time variable t is set to zero, and the variables min and max are set to their initial values. These are the most positive and most negative values, respectively, that the control system can numerically represent. For the 8-bit words used in the preferred embodiment MAX_INIT is −127 and MIN_INIT is +128. After initialization, the pulse waveform is sampled at step 264, and the timer t is incremented. In the preferred embodiment the waveform is sampled at 100 Hz, so that DELTA_T represents 10 msec. The value of the sample is tested against the current maximum at step 266 and current minimum at step 270. If the sample is greater than the current maximum then the current maximum is replaced with the present sample's value and the time of the new maximum is recorded, step 268. On the other hand, if the sample is less than the current minimum then the current minimum is replaced with the present sample's value and the time of the new minimum is recorded, step 272. At step 274, the time that has elapsed since the most recent ventricular depolarization, t, is compared against a preset value, SEARCH_DURATION. In the preferred embodiment this value represents 200 msec. If t is less that SEARCH_DURATION, then control returns to step 264 and the search for the maximum and minimum continues. Otherwise, an error check is made at step 276. With the narrow-band filtering used in the preferred embodiment, the maximum of the plethysmography waveform should occur earlier than the minimum. If this condition is not satisfied, then it is concluded that the signal is corrupted by motion artifact. In this case, the error flag is set at step 278, a backup safety pulse is delivered at step 280, and the algorithm terminates for the present cardiac cycle at step 282. On the other hand, if the timing criterion is satisfied at step 276, then the pulse amplitude is calculated at step 284. If the calculated pulse amplitude does not exceed a predetermined threshold HD_THRESH, which represents a hemodynamically sufficient contraction, then a backup safety pulse is delivered at step 288. A further test against noise and motion artifact is made over the remainder of the cardiac cycle, the results of which are made available to the higher-level control algorithm. The test is performed by determining a new maximum and minimum over the remainder of the present cardiac cycle. Any local maxima and minima in this region of the cardiac cycle should be small in amplitude, below the predetermined thresholds MAX_THRESH and MIN_THRESH. Continuing with the algorithm, the variables max and min are reinitialized to their starting values at step 290. The waveform is sampled at step 292. If the sample is greater than the present maximum, step 294, then max is updated with the present sample, step 296. If the sample is less than the present minimum, step 298, then min is updated with the present sample, step 300. If a QRS complex or ventricular depolarization is not detected or it is not time for the next pace pulse, step 302, then control returns to step 292 and a new sample is obtained. Otherwise, the variable max is compared against the predetermined threshold MAX_THRESH at step 304, and if it exceeds the threshold, a noise or motion artifact is deemed to have occurred. In this case the error flag is set, step 306. Similarly, the variable min is compared against the predetermined threshold MIN_THRESH at step 308, and if it exceeds the threshold in the negative sense, a noise or motion artifact is deemed to have occurred. In this case the error flag is set at step 310. The algorithm terminates at step 312. A higher level algorithm intermittently decrements the pacing voltage if capture is consistently successful, and increments the pacing voltage if capture fails.

In an alternate embodiment capture verification is performed in the analog domain. The delivery of a pacing pulse resets a timer which, after a predetermined duration such as 150 msec, delivers an interrupt which causes the device to deliver a rescue pace pulse. The interrupt is disabled by the detection of a hemodynamically significant systolic pulse or contraction. This detection is performed using an analog comparator between the output of a hemodynamic sensor, such as an optical plethysmography sensor or heart sound sensor, and a predetermined threshold. This alternate embodiment is advantageous in that it does not require operation of the power-consuming microprocessor or analog to digital converter, however, it is less amenable to noise and motion artifact detection than the preferred embodiment.

More complex algorithms record the recent history of the pulse amplitude, or maintain recent statistics, such as mean and variability. Other embodiments of pulse measurement with or without motion artifact or noise detection are possible. One specific alternative is to take the value of the maximum above the baseline as a measure of pulse amplitude. This reduces the number of variables and comparisons at the risk of reducing the precision of the pulse measurement.

In another alternate embodiment an accelerometer within the device is used to detect motion. To avoid spurious readings due to motion artifact the optical sensor is not used in the presence of motion. Rather, arrhythmia discrimination is performed using conventional electrogram analysis.

In yet another alternate embodiment systolic pulses are detected using a template matching algorithm, such as cross correlation or other correlation measure. An excursion of the plethysmography signal beyond a predetermined threshold above baseline initiates the calculation of the cross correlation function between the stored plethysmography template for a systolic pulse and the current waveform. If the correlation is not sufficiently large, then noise is deemed to be responsible for the excursion and the hemodynamic sensor output is invalidated.

In still another alternate embodiment, detection of an arterial pulse and detection of noise or motion artifact are performed in analog circuitry. The crossing of a threshold, predetermined to be lower than a hemodynamically stable systolic pulse but significantly higher than the noise floor, is detected in analog circuitry using a comparator. The threshold crossing causes the contents of a free-running timer to be copied to a register which contains the history of intervals between detected pulses. This information can be used alone or in conjunction with sensed electrical activity to determine whether an arrhythmia is present which requires electrical therapy. It can also be used to optimize electrical sensing threshold and gain settings and verify that a previously delivered pacing pulse successfully captured the myocardium. Since this approach does not retain the strength of the systolic contraction it cannot be used for pace parameter optimization.

In yet another alternate embodiment, a peak detector is used in analog circuitry to capture the maximum and/or minimum excursion of the pulse waveform. An electrical marker such as QRS complex or delivered pace pulse can be used to reset the peak detector at the beginning of each cardiac cycle. This advantageously requires only one or two A/D conversions per cardiac cycle, depending on the embodiment, in contrast to one every 10 msec in the case of the preferred embodiment. Furthermore, it greatly reduces the number of arithmetic operations, thereby reducing energy consumption.

Although presently preferred embodiments of the present invention have been described in detail hereinabove, it should be clearly understood that many variations and/or modifications of the basic inventive concepts herein taught, which may appear to those skilled in the pertinent art, will still fall within the spirit and scope of the present invention, as defined in the appended claims.

What is claimed is:

1. An implantable medical device including a sensor for use in detecting the hemodynamic status of a patient comprising:

a hermetic device housing enclosing device electronics for receiving and processing data;

said device housing including at least one substantially planar face configured to act as a diaphragm in response to acoustic waves; and a transducer positioned inside said device housing to provide an output signal to said device electronics responsive to vibration of said diaphragm.

2. The implantable medical device of claim 1 wherein said transducer comprises a piezoelectric element positioned on said diaphragm.

3. The implantable medical device of claim 1 wherein said transducer comprises a laser interferometery source and detector having a laser light reflecting off of said diaphragm.

4. An implantable medical device including a hemodynamic sensor for monitoring pulse amplitude comprising:

a device housing; and a transducer comprising a laser interferometer positioned inside said device housing responsive to heart sounds.

5. An implantable medical device comprising:

a device housing;

a transducer associated with said device housing responsive to heart sounds;

electronic circuitry for controlling said medical device and coupled to receive sensed heart sound signals from said transducer and for processing said sensed heart sound signals and controlling said device in response thereto; and an accelerometer wherein said accelerometer detects motion artifacts that could interfere with said sensed heart sound signals.

6. The medical device of claim 5 wherein said electronic circuitry uses said sensed heart sound signals to discriminate among possible cardiac arrhythmias.

7. The medical device of claim 5 wherein said sensed heart sound signals are analyzed for the presence of noise artifacts.

8. The medical device of claim 5 wherein said medical device is an implantable pulse generator for providing pacing therapy to a patient's heart and wherein said electronic circuitry uses said sensed heart sound signals to optimize the timing of pacing pulses provided to said patient's heart.

9. An implantable pulse generator for providing pacing therapy to a patient's heart comprising:

a device housing;

a transducer associated with said device housing responsive to heart sounds;

a posture sensor; and electronic circuitry to control said pulse generator coupled to receive sensed heart sound signals from said transducer and posture sensor signals from said posture sensor, said electronic circuitry processing said sensed heart sound signals and said posture signal wherein the timing of pacing pulses provided to said patient's heart is optimized using said sensed heart sound signals upon sensing of a change of the patient's posture by said posture sensor.

10. An implantable medical device comprising:

a device housing;

a sensing lead for coupling to said patient's heart to sense electrical signals from the heart;

a transducer associated with said device housing responsive to heart sounds; and electronic circuitry to control said medical device and coupled to receive sensed heart sound signals from said transducer, said electronic circuitry processing said sensed heart sound signals;

wherein said electronic circuitry uses said sensed heart sound signals to optimize electrical sensing with said sensing lead.

* * * * *